(12) United States Patent
Mechoulam et al.

(10) Patent No.: US 7,884,133 B2
(45) Date of Patent: Feb. 8, 2011

(54) PHARMACEUTICAL COMPOSITIONS CONTAINING (+) CANNABIDIOIL AND DERIVATIVES THEREOF AND SOME SUCH NOVEL DERIVATIVES

(75) Inventors: Raphael Mechoulam, Jerusalem (IL); Ester Fride, Elkana (IL)

(73) Assignees: Yissum Research Development Company of the Hebrew University of Jerusalem, Jerusalem (IL); Ariel Ltd., Ariel (IL)

( * ) Notice: Subject to any disclaimer, the term of this patent is extended or adjusted under 35 U.S.C. 154(b) by 1133 days.

(21) Appl. No.: 10/570,737

(22) PCT Filed: Sep. 8, 2004

(86) PCT No.: PCT/IL2004/000810
§ 371 (c)(1),
(2), (4) Date: Sep. 28, 2006

(87) PCT Pub. No.: WO2005/023741
PCT Pub. Date: Mar. 17, 2005

(65) Prior Publication Data
US 2007/0082954 A1    Apr. 12, 2007

(30) Foreign Application Priority Data
Sep. 10, 2003   (IL)   ..................... 157849

(51) Int. Cl.
A61K 31/19      (2006.01)
A61K 31/075     (2006.01)
A61K 31/045     (2006.01)
A61K 31/05      (2006.01)
C07C 63/00      (2006.01)
C07C 39/00      (2006.01)
C07C 43/115     (2006.01)

(52) U.S. Cl. ........................ 514/568; 514/719; 514/729; 514/731; 562/469; 568/743; 568/763; 568/660

(58) Field of Classification Search ........................ None
See application file for complete search history.

(56) References Cited

U.S. PATENT DOCUMENTS 6,630,507 B1 * 10/2003 Hampson et al. ............. 514/454
2003/0166727 A1 * 9/2003 Mechoulam et al. ......... 514/568
2007/0099987 A1 * 5/2007 Weiss et al. .................. 514/454

FOREIGN PATENT DOCUMENTS

WO        01/95899 A2    12/2001

OTHER PUBLICATIONS

Bisogno et al., 134 Br. J. Pharmacol., 845-852 (2001).*
Bisogno et al., 134 Brit. J. Pharm., 845-52 (2001).*
Database CAPLUS on STN, Acc. No. 1978:608839, Harvey et al., Recent Dev. Mass Spectrom. Biochem. Med., [Proc. Int. Symp.], 4$^{th}$ (1978), Meeting Date 1977, vol. 1, p. 161-184 (abstract).*
Database CAPLUS on STN, Acc. No. 2001:834237, Bisogno et al., British Journal of Pharmacology (2001), 134(4), p. 845-852 (abstract).*
Bisogno, Tiziana et al., British Journal of Pharmacology, 134 (4):845-852 (2001) XP002319199.
Casu, M. A. et al. (2003) Eur. J. Pharmacol. 459(1): 97-105.
Chesher, G. B. et al. (1973) Br. J. Pharmacol. 49(4): 588-94.
Colombo, G. et al. (1998) Eur. J. Pharmacol. 344(1): 67-9.
Fride, E. (1995) Brain Res. 697, 83.
Fride, E. and R. Mechoulam (1993) Eur. J. Pharmacol. 231, 313.
Galiegue, S. et al. (1995) Eur. J. Biochem. 232(1): 54-61.
Gardner, A.L. et al. (1988) Trends Pharmacol. Sci. Suppl.: 40-3.
Griffin, G. et al. (1997) Eur. J. Pharmacol. 339, 53.
Gurwitz, D. et al. (1994) Eur. J. Pharmacol. 267, 21.
Haefely, W. et al. (1990) Trends Pharmacol. Sci. 11(11): 452-6.
Hanus, L. et al. (1999) Proc. Natl. Acad. Sci. USA 96, 14228.
Herkenham, M. (1995) Cannabinoid receptors, London, Academic Press: 145-166.
Izzo, A. et al. (2000) Br. J. Pharmacol. 129(8): 1627-32.
Izzo, A.A. et al. (2001) Br. J. Pharmacol. 132, 1411.
Johnson, M.R. and Melvin, L.S. (1986) The discovery of non-classical cannabinoids analgetics. In: Cannabinoids as therapeutic agents. Ed. R. Mechoulam, CRS Press FL, pp. 121-145.
Landi, M. et al. (2002) Eur. J. Pharmacol. 450, 77.

(Continued)

Primary Examiner—Brian J Davis
(74) Attorney, Agent, or Firm—Roach Brown McCarthy & Gruber, P.C.; Kevin D. McCarthy

(57) ABSTRACT

Cannabinoid derivatives are known for their function in the central as well as peripheral nervous system. Disclosed are some novel (+)-cannabidiol (CBD) derivatives of the general formula (I)

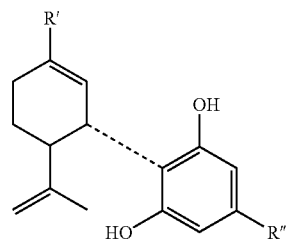

having selective activity in the peripheral, but not in the central nervous system. Use of (+)-CBD derivatives as analgesics, anti-inflammatory and anti-diarrheal agents is also disclosed.

4 Claims, 13 Drawing Sheets

OTHER PUBLICATIONS

Malfait, A.M. et al. (2000) Proc. Natl. Acad. Sci. USA 97, 9561.
Martin, B. R. et al. (1991) Pharmacol. Biochem. Behav. 40(3): 471-8.
Mechoulam, R. et al. (1998) Prog. Med. Chem. 35, 199.
Parker, L.A. et al. (2002) Neuroreport 13, 567.
Pertwee, R.G. (1997) Pharmacol. Ther. 74, 129.
Pertwee, R.G. (2001) Gut 48(6): 859-67.
Pinto, L. (2002) Prostaglandins Leukot Essent Fatty Acids 66, 333.
Robson, P. (2001) Br. J. Psychiatry 178, 107.
Tjolsen, A. and Hole (1997) The Pharmacology of Pain, Springer, Heidelberg, pp. 1-20].
Young, J. M. et al. (1984) J. Invest. Dermatol. 82, 367-71.

* cited by examiner

PHARMACEUTICAL COMPOSITIONS CONTAINING (+) CANNABIDIOIL AND DERIVATIVES THEREOF AND SOME SUCH NOVEL DERIVATIVES

FIELD OF THE INVENTION

The present invention relates to the use of (+)-cannabidiol derivatives as activators of the peripheral cannabinoid system and to some such novel (+)-cannabidiol derivatives. The (+)-cannabidiol derivatives of the invention do not activate the central nervous system, particularly the brain, and are thus devoid of psychoactive side effects. Therefore the (+)-cannabidiol derivatives of the invention are particularly useful as modulators/regulators of the immune system and the gastrointestinal tract.

BACKGROUND OF THE INVENTION

All publications mentioned throughout this application are fully incorporated herein by reference, including all references cited therein.

Delta-9 tetrahydrocannabinol ($\Delta$9-THC) and (−)-cannabidiol (CBD) are the two major constituents of the *Cannabis sativa* (marihuana) plant. $\Delta$9-THC is psychoactive and binds to cannabinoid $CB_1$ receptors located in the brain and the periphery [Herkenham, M. (1995) *Cannabinoid receptors*, London, Academic Press: 145-166; Pertwee, R. G. (1997) *Pharmacol. Ther.* 74, 129], as well as to $CB_2$ receptors which are located exclusively on non-neural tissue, such as immune cells [Pertwee (1997) id. ibid.]. CBD binds neither receptor and is not psychoactive. $\Delta$9-THC is considered to be responsible for virtually all central effects observed with the cannabis plant and for many of its peripheral effects [Pertwee (1997) id. ibid.; Mechoulam, R. et al. (1998) *Prog. Med. Chem.* 35, 199; Fride, E. and C. Sanudo-Pena (2002) Cannabinoids and endocannabinoids: behavioral and developmental aspects. In: The Biology of Marijuana, ed. E. Onaivi, Harwood Academic Publishers, Reading]. Peripheral effects include inhibition of gastrointestinal activity [Pinto, L. (2002) *Prostaglandins Leukot Essent Fatty Acids* 66, 333] and anti-inflammatory effects [Mechoulam (1998) id. ibid.].

In view of the abundance of $CB_1$ and $CB_2$ receptors on immune cells [Galiegue, S. et al. (1995) *Eur. J. Biochem.* 232(1): 54-61; Pertwee (1997) id. ibid.], it is not surprising that cannabinoids are effective regulators of the inflammatory process including peripheral pain [Hanus, L. et al. (1999) *Proc. Natl. Acad. Sci.* USA 96, 14228; Mechoulam (1998) id. ibid.; Malfait, A. M. et al. (2000) *Proc. Natl. Acad. Sci.* USA 97, 9561].

There is ample evidence in vitro and in vivo for an inhibitory action of $\Delta$9-THC and other cannabinoids and endocannabinoids (anandamide, 2-arachidonoyl glycerol, 2-AG and noladine ether, see [Fride, E. (2002) *Endocannabinoids in the central nervous system—an overview. Prostaglandins, Leukotrienes and Essential Fatty Acids*.] on intestinal motility in various species such as mice, rats and guinea pigs [Pertwee (1997) id. ibid; Pinto (2002) id. ibid.]. Early work includes in vivo evidence for an inhibitory effect of $\Delta$9-THC on intestinal motility in mice [Chesher, G. B. et al. (1973) *Br. J. Pharmacol.* 49(4): 588-94]. Endocannabinoid-induced inhibition of intestinal motility was first demonstrated for anandamide as a near cessation of defecation in mice [Fride, E. and R. Mechoulam (1993) *Eur. J. Pharmacol.* 231, 313; Fride, E. (1995) *Brain Res.* 697, 83].

Most evidence suggest that the cannabinoid-induced gastrointestinal inhibition is mediated by $CB_1$ receptors [Colombo, G. et al. (1998) *Eur. J. Pharmacol.* 344(1): 67-9; Pertwee, R. G. (2001) *Gut* 48(6): 859-67, Pinto, L. (2002) *Prostaglandins Leukot Essent Fatty Acids* 66, 333; Calignano, A. et al. (1973) *Br J Pharmacol* 49, 588]. This is in agreement with a presence of $CB_1$ receptors and $CB_1$ receptor mRNA [Casu, M. A. et al. (2003) *Eur. J. Pharmacol.* 459(1): 97-105; Griffin, G. et al. (1997) *Eur. J. Pharmacol.* 339, 53], but not of $CB_2$ receptor mRNA in the mesenteric plexus of the gut. It has also been determined that gastrointestinal transit is regulated locally in the periphery rather than by centrally located $CB_1$ receptors [Izzo, A. et al. (2000) *Br. J. Pharmacol.* 129(8): 1627-32; Landi, M. et al. (2002) *Eur. J. Pharmacol.* 450, 77].

On the other hand, the inventors have shown previously that the selective $CB_2$ receptor agonist, HU-308, inhibited defecation which was antagonized by the selective $CB_2$ receptor antagonist SR144528, but not by the $CB_1$ receptor antagonist SR141716A [Hanus (1999) id. ibid.].

These findings suggest that cannabinoids may be developed as therapeutic agents in conditions such as inflammatory pain and inflammatory bowel diseases. The significant drawback for the use of cannabis or $\Delta$9-THC is the unwanted psychoactive side effects, such as anxiety, confusion and memory impairment, which may be observed with higher doses [Robson, P. (2001) *Br. J. Psychiatry* 178, 107]. Therefore current efforts are aimed at developing cannabinoids with medical benefits but which are devoid of psychoactive side effects.

Despite the dichotomy between $\Delta$9-THC and CBD, CBD displays a number of pharmacological activities, which are similar to those of $\Delta$9-THC. These include anti-emetic [Parker, L. A. et al. (2002) *Neuroreport* 13, 567] and anti-inflammatory effects [Malfait, A. M. et al. (2000) *Proc. Natl. Acad. Sci.* USA 97, 9561]. Being devoid of psychoactive effects, CBD is a good candidate for future development of peripherally acting cannabinoid-like drugs.

The present inventors have previously described several (−)-CBD derivatives and their activity as anti-inflammatory agents, analgesics, neuroprotective and antipsychotic as well as anti-cancer agents [WO 01/95899]. This publication also describes the synthesis of the (−)-(CBD) derivatives. Other derivatives, which contain etheric groups, were described in the review of Johnson and Melvin [Johnson, M. R. and Melvin, L. S. (1986) The discovery of non-classical cannabinoids analgetics. In: *Cannabinoids as therapeutic agents*. Ed. R. Mechoulam, CRS Press Fl., pp. 121-145].

In a previous report [Bisogno et al. (2001) id ibid], the inventors described the biochemical properties of a number of derivatives of the natural (−)-CBD as well as the synthetic (+)-CBD, namely (+)-CBD-DMH and (+)-7-OH-CBD-DMH. Only the latter (+) analogues were found to bind $CB_1$ and/or $CB_2$ receptors. Vannilloid VR1 receptors or increased levels of the endocannabinoid anandamide may mediate effects of some, but not all analogues. Based on such findings, candidates for anti-inflammatory or other therapeutic activity may be developed.

In search for selective agonists/antagonists of the peripheral cannabinoid system, which would not affect the central nervous system, which are an object of the present invention, the inventors examined the aforementioned (+)-CBD, (+)-CBD-DMH and (+)-7-OH-CBD-DMH, and several novel (+)CBD analogues, particularly (+)-7-OH-CBD, (+)-COOH-CBD and (+)-COOH-CBD-DMH), for central as well as peripheral activity in mice. Some synthetic (+)-CBD derivatives were indeed found to possess such selective activity.

It is therefore an object of the present invention to provide (+)-CBD derivatives for use as selective modulators of the peripheral nervous system. Further objects of the present invention are to provide (+)-CBD derivatives for use as analgesics, anti-inflammatory and anti-diarrheal agents.

It is a further object of the present invention to provide novel (+)-CBD derivatives, which may be useful as selective modulators of the peripheral nervous system.

These and other objects of the invention will become apparent as the description proceeds.

SUMMARY OF THE INVENTION

The present invention relates to an optically pure (+) enantiomer of a compound of the formula:

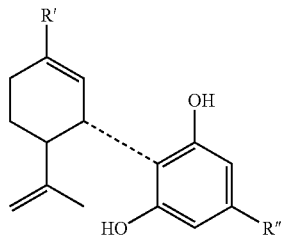

Formula I wherein:
R' designates a —COOH or —CH$_2$OH group, and
R" designates (i) a straight or branched C$_5$-C$_{12}$ alkyl group, or (ii) an —OR''' group wherein R''' designates a straight or branched C$_5$-C$_9$ alkyl group which may be optionally substituted with a phenyl group on the terminal carbon atom, or (iii) a —(CH$_2$)$_n$—O—C$_{1-5}$ alkyl group, wherein n is an integer of from 1 to 7;

with the proviso that R' is not —CH$_2$OH when R" is pentyl or dimethylheptyl, and pharmaceutically acceptable salts and esters thereof.

In preferred compounds, R' is —COOH and R" is a pentyl or dimethylheptyl group.

The invention also relates to a pharmaceutical composition containing as active ingredient a compound of formula I wherein the substituents are defined as above, and optionally further comprising at least one pharmaceutically acceptable carrier, additive, excipient or diluent. The pharmaceutical composition of the invention may optionally further comprise an additional pharmaceutically active agent.

In a further aspect the invention relates to the use of a (+) enantiomer of a compound of the formula:

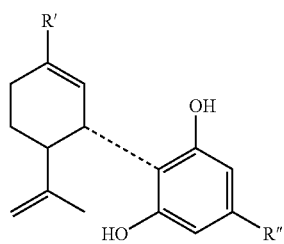

Formula Ia wherein:
R' designates a —COOH or —CH$_2$OH group, and
R' designates (i) a straight or branched C$_5$-C$_{12}$ alkyl group, or (ii) an —OR''' group wherein R''' designates a straight or branched C$_5$-C$_9$ alkyl group which may be optionally substituted with a phenyl group on the terminal carbon atom, or (iii) a —(CH$_2$)$_n$—O—C$_{1-5}$ alkyl group, wherein n is an integer of from 1 to 7, or a pharmaceutically acceptable salt or ester; as a selective modulator of the peripheral cannabinoid system.

Preferably, the (+) enantiomer of a compound of formula Ia is used as an analgesic agent, a modulator of the immune system, an anti-inflammatory agent, or as a modulator of the gastrointestinal tract, particularly an anti-diarrheal agent.

The invention further relates to the use of a (+) enantiomer of a compound of the formula (Ia) wherein the substituents are as defined above or a pharmaceutically acceptable salt or ester thereof, in the preparation of a pharmaceutical composition for the selective treatment of disorders associated with the peripheral cannabinoid system.

In particular embodiments, the pharmaceutical compositions prepared in accordance with the invention are analgesic pharmaceutical compositions, pharmaceutical compositions for the treatment of immune disorders associated with the peripheral cannabinoid system, anti-inflammatory compositions, and pharmaceutical compositions for the treatment of a disorder associated with the gastrointestinal tract, particularly an anti-diarrheal pharmaceutical composition.

The invention further relates to methods of treatment of disorders associated with the peripheral cannabinoid system by administering to a subject in need of such treatment a therapeutically effective amount of a compound of formula Ia or of a pharmaceutical composition in accordance with the invention.

The invention will be described in more detail on hand of the following figures.

(+)-CBD was injected (20 mg/kg) i.p. into female Sabra mice. Sixty minutes later, the animals were tested for effects in the central (FIGS. 1A-1E) and peripheral (FIG. 1F) nervous system.

Figure 1A:
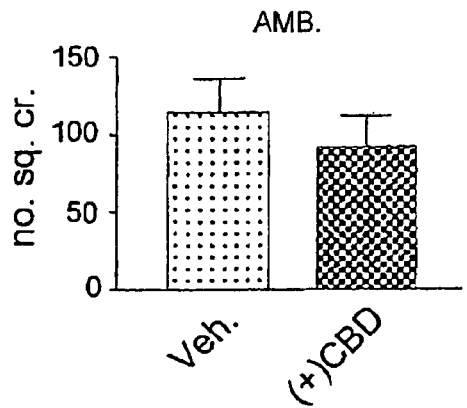
FIGS. 1A-F: Lack of effects of (+)-CBD.
Figure 1B:
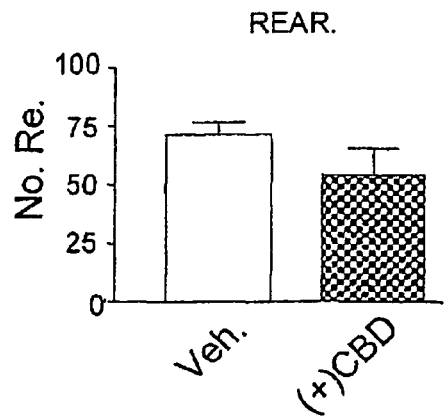
Figure 1C:
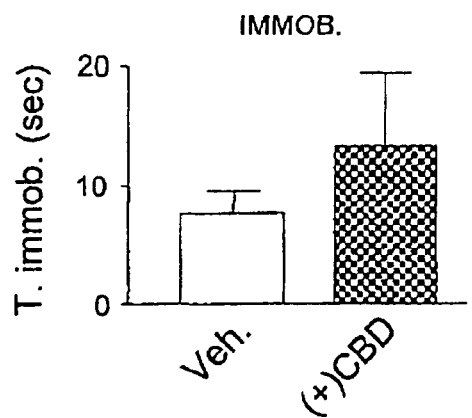
Figure 1D:
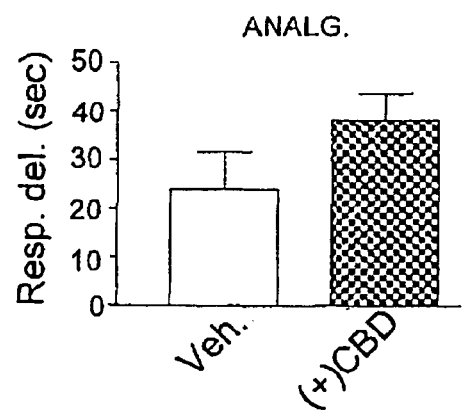
Figure 1E:
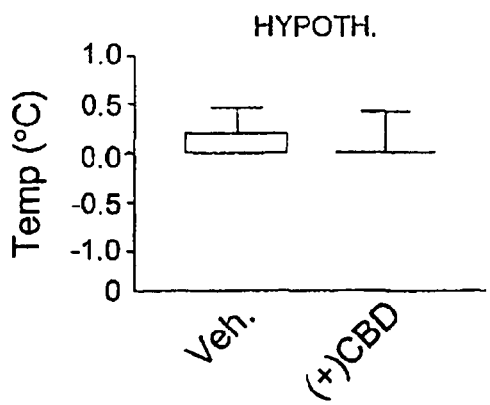
Figure 1F:
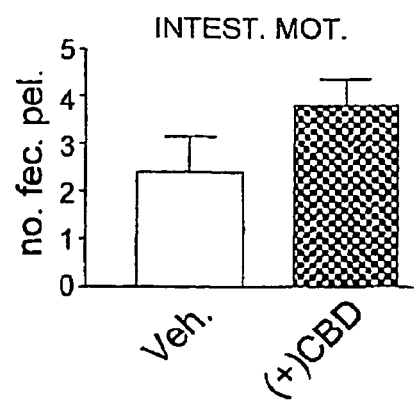

FIG. 1A: Ambulation in an open field.
FIG. 1B: Rearing in an open field.
FIG. 1C: Immobility on a ring.
FIG. 1D: Hot plate analgesia.
FIG. 1E: Hypothermia.
FIG. 1F: Intestinal motility.

Abbreviations: Amb., ambulation; no. sq. cr., number of squares crossed; Rear., rearing; No. Re., number of rears; Immob., immobility; t. immob.; time immobile; Analg., analgesia; resp. del., response delay; Hypoth., hypothermia; Intest. Mot., intestinal motility; no. fec. pel., number of fecal pellets; Temp., temperature; veh., vehicle.

FIGS. 2A-D: Central cannabinoid effects.

(+)-7-OH-CBD, (+)-7-OH-CBD-DMH, (+)-COOH-CBD, (+)-COOH-CBD-DMH and (+)-CBD-DMH (20 mg/kg) were injected i.p. into female Sabra mice. Mice were tested 60 minutes later for centrally mediated effects.

Figure 2A:
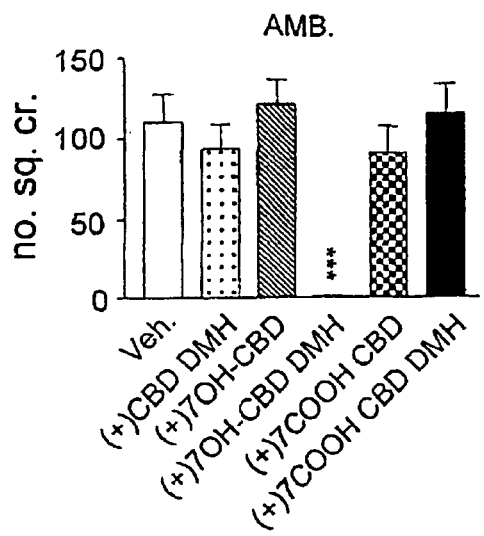
Figure 2B:
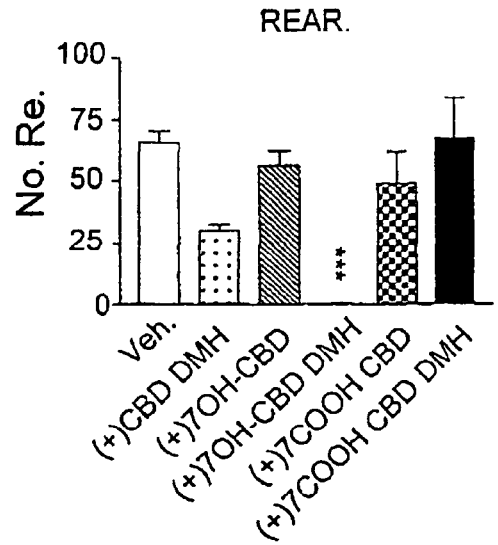
Figure 2C:
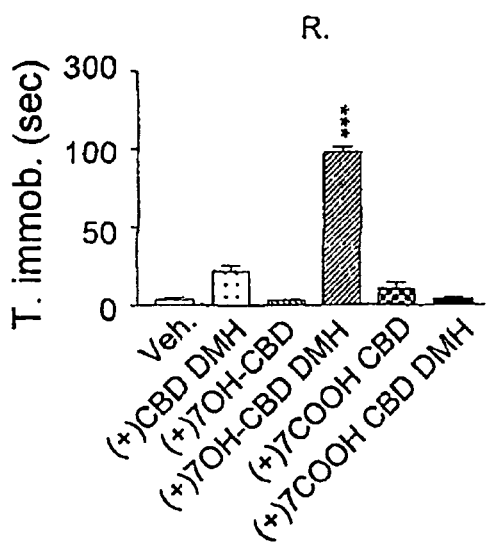
Figure 2D:
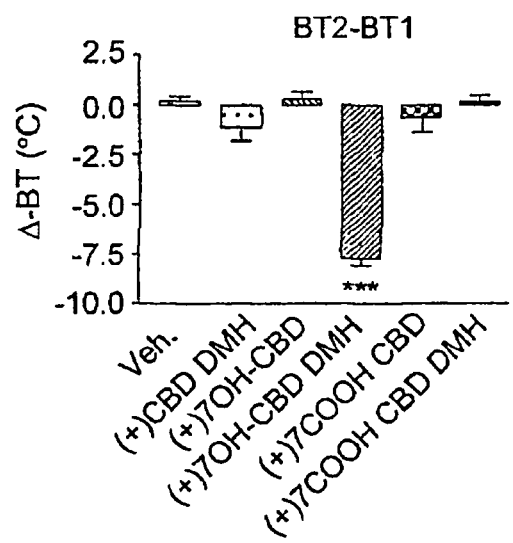

FIG. 2A: Ambulation in an open field.
FIG. 2B: Rearing in an open field.
FIG. 2C: Catalepsy (immobility) on an elevated ring.
FIG. 2D: Hypothermia.

(+)7OH-CBD-DMH was very potent whereas none of the other (+)CBD derivatives had any effect.

***) P<0.001 cf. Vehicle-injected mice.

Abbreviations: Amb., ambulation; no. sq. cr., number of squares crossed; Rear., rearing; No. Re., number of rears; R., ring; T. immob., time immobile; veh., vehicle.

Figure 3A:
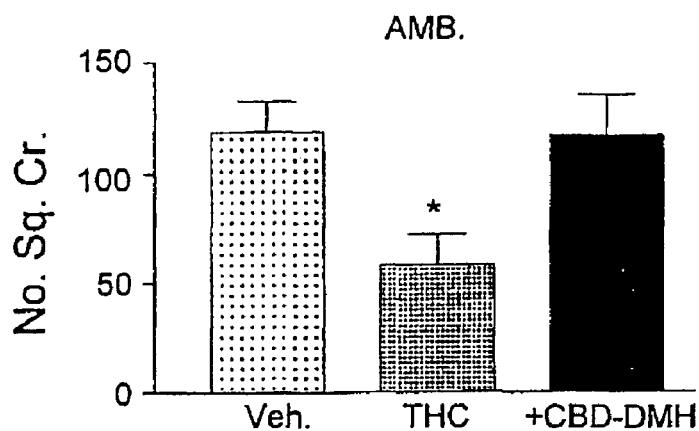
Figure 3B:
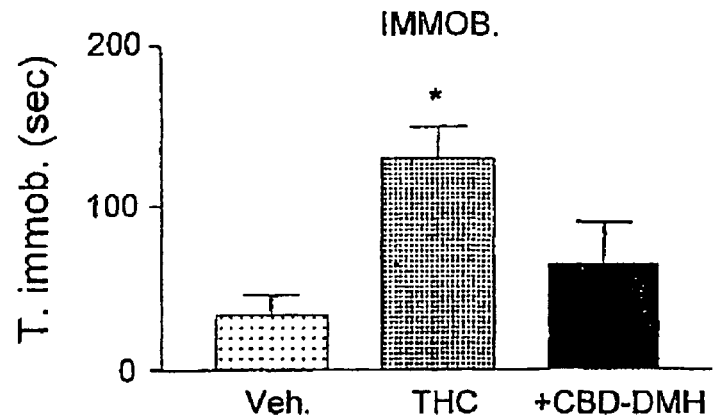
Figure 3C:
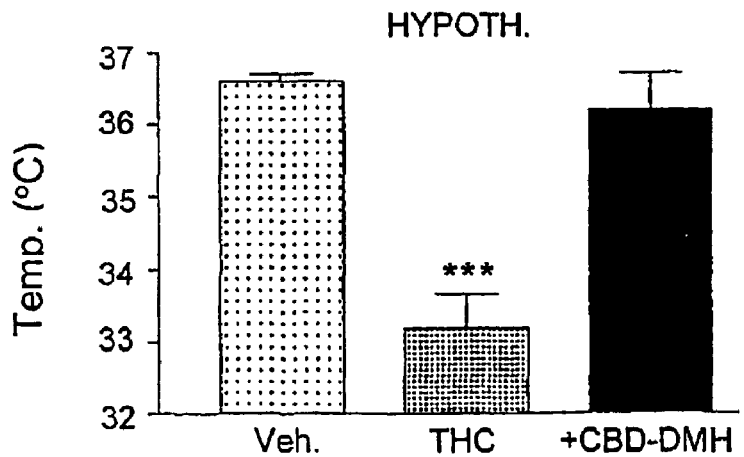

FIGS. 3A-C: Lack of central effects of (+)-CBD-DMH using THC as a reference drug.

Both drugs were injected i.p. at a dose of 20 mg/kg (see Legend of FIG. 2 for full explanations).

FIG. 3A: Ambulation in an open field.

FIG. 3B: Catalepsy (immobility) on an elevated ring.

FIG. 3C: Hypothermia.

\*) $P<0.05$ cf Vehicle; \*\*\*) $P<0.001$ cf Vehicle.

Abbreviations: Amb., ambulation; no. sq. cr., number of squares crossed; Immob., immobility; t. immob.; time immobile; Hypoth., hypothermia; Temp., temperature; veh., vehicle.

Figure 4:
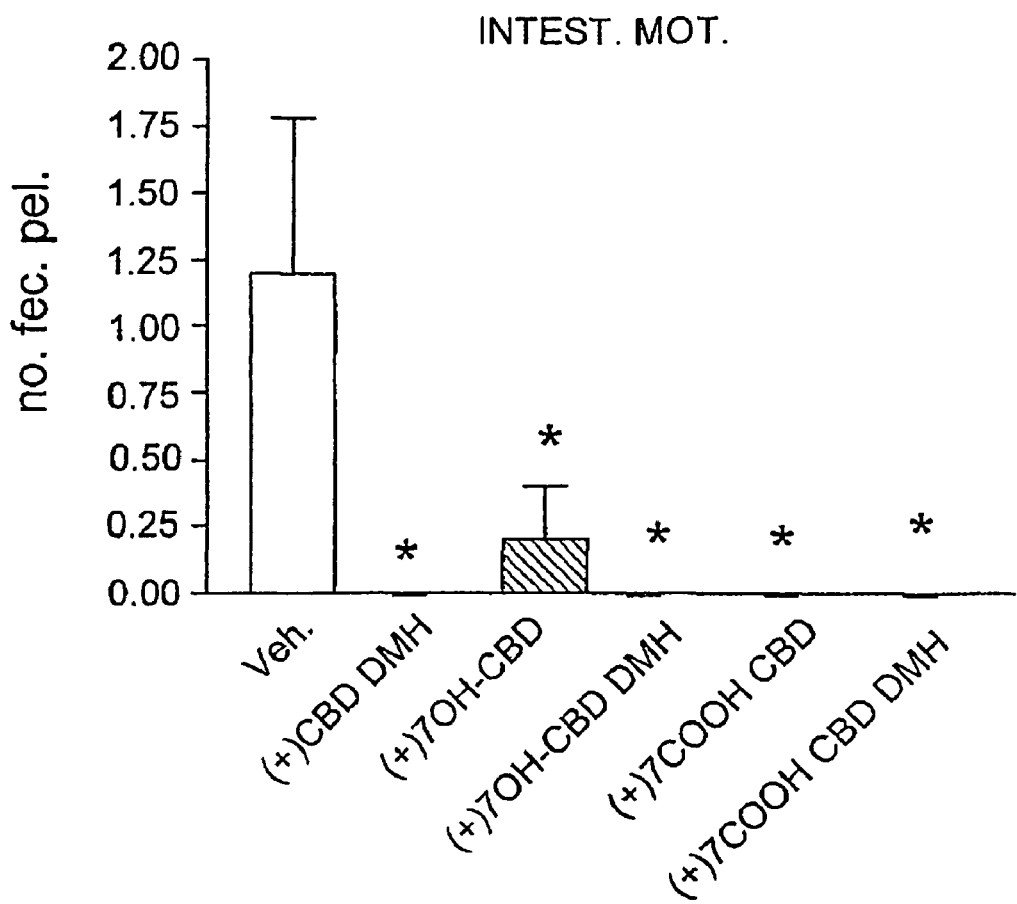

FIG. 4: Inhibition of Intestinal Motility.

Sixty minutes after i.p. injections of (+)-CBD-DMH or (+)-7-OH-CBD-DMH, defecation (intestinal motility) was completely blocked.

\*\*\*) different from vehicle control ($P<0.001$).

Abbreviations: Intest. Mot., intestinal motility; no. fec. pel., number of fecal pellets; veh., vehicle.

Figure 5A:
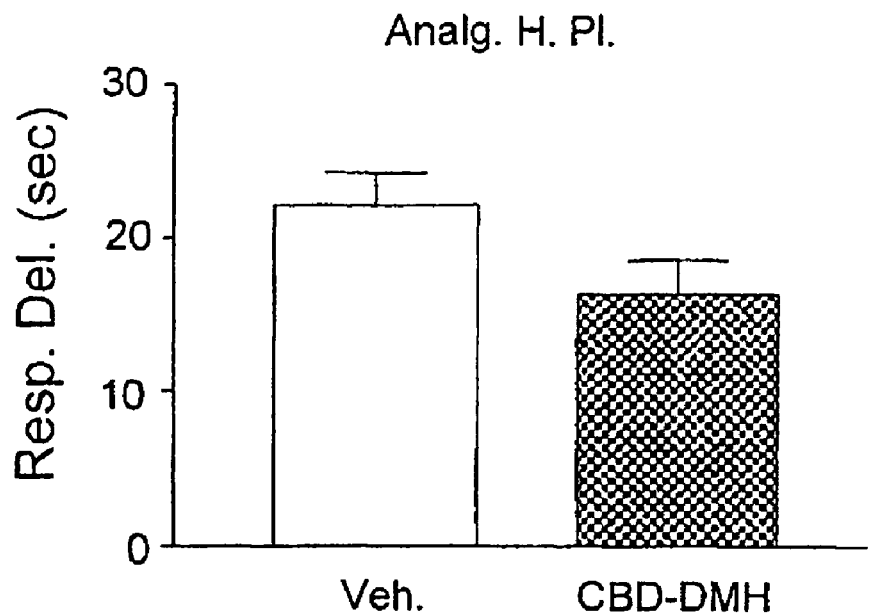
Figure 5B:
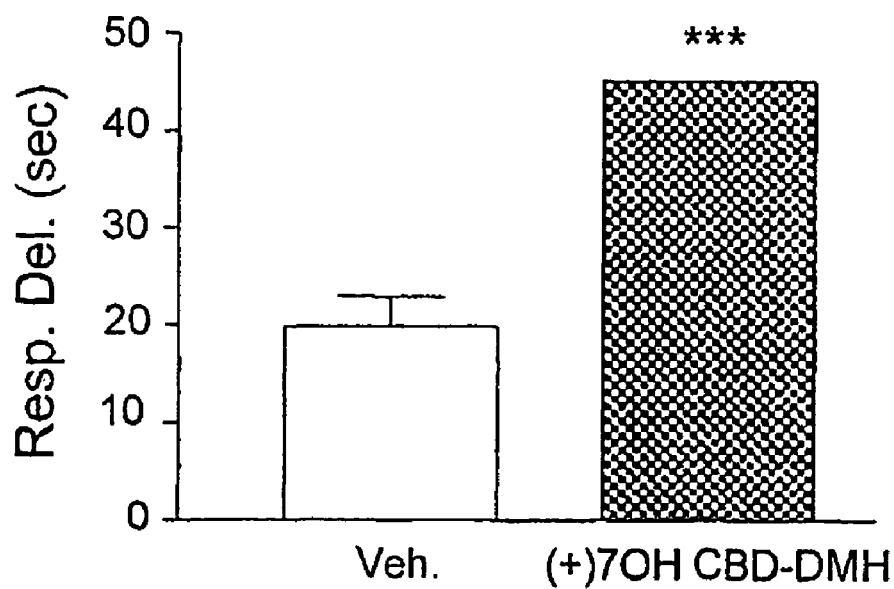

FIGS. 5A-B: Lack of centrally mediated analgesia on hot plate.

FIG. 5A: By (+)CBD-DMH (20 mg/kg).

FIG. 5B: By (+)OH-CBD-DMH (B) (20 mg/kg).

\*\*\*) $P<0.001$ vs. control (vehicle)

Abbreviations: Analg. H. P., analgesia on a hot plate; resp. del., response delay; veh., vehicle.

Figure 6:
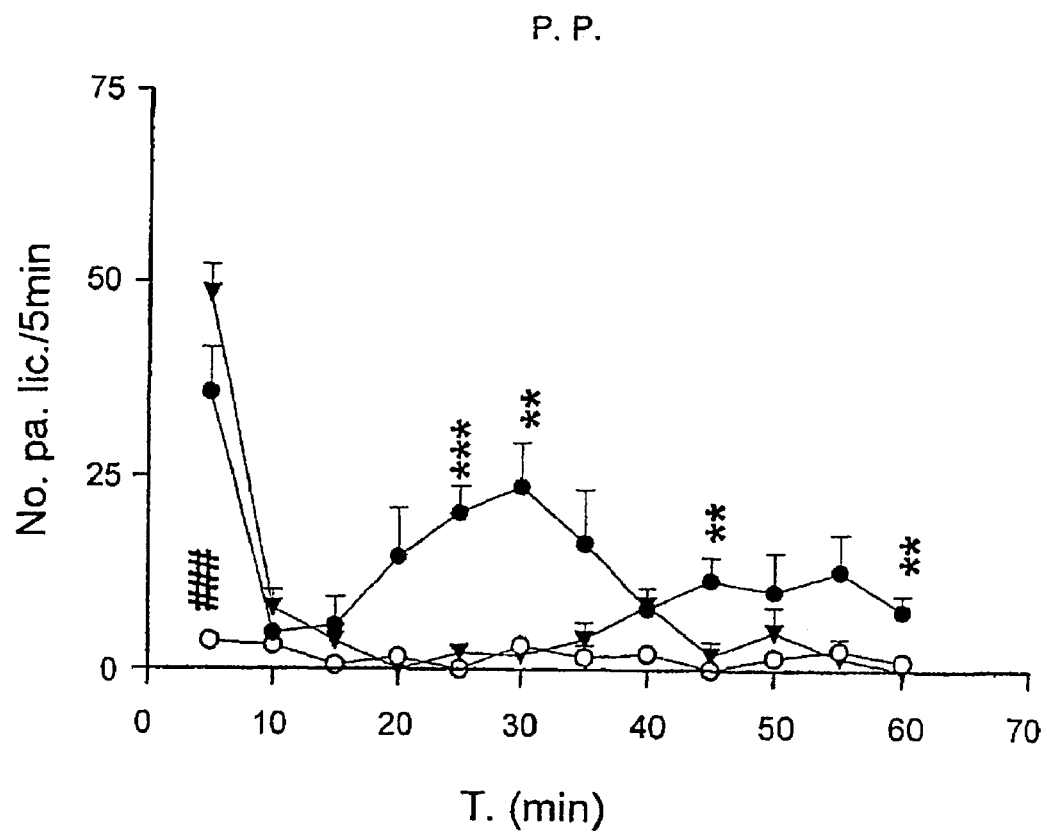

FIG. 6: Analgesic effect of (+)-CBD-DMH in a model of non-centrally mediated pain.

Formalin (4%) was injected in the left hind footpad and the number of licks of the injected foot were recorded for each 5 minutes interval for the 60 minutes starting immediately after formalin application. (+)-CBD-DMH almost completely prevented the second phase of pain.

Abbreviations: P. P., peripheral pain; no. pa. lic., number of paw licks; T., time.

Figure 7A:
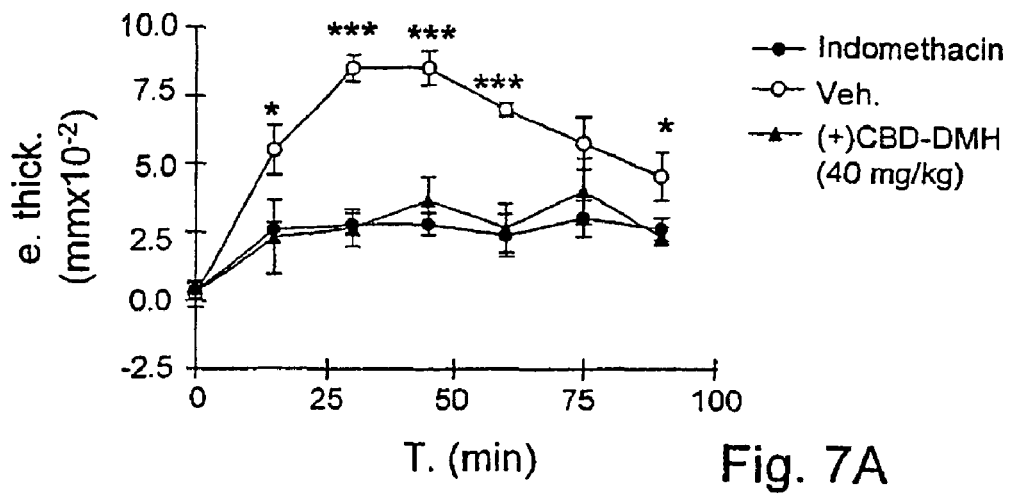
Figure 7B:
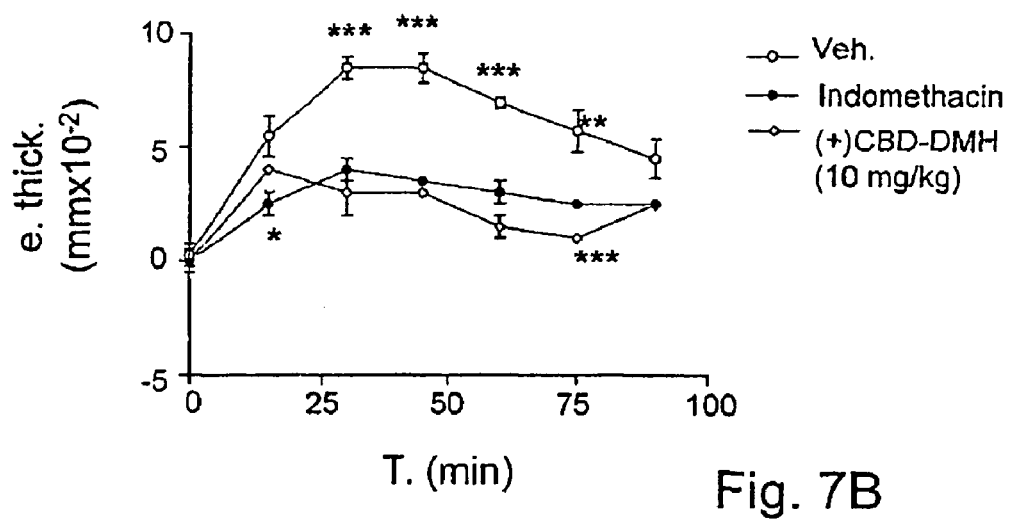
Figure 7C:
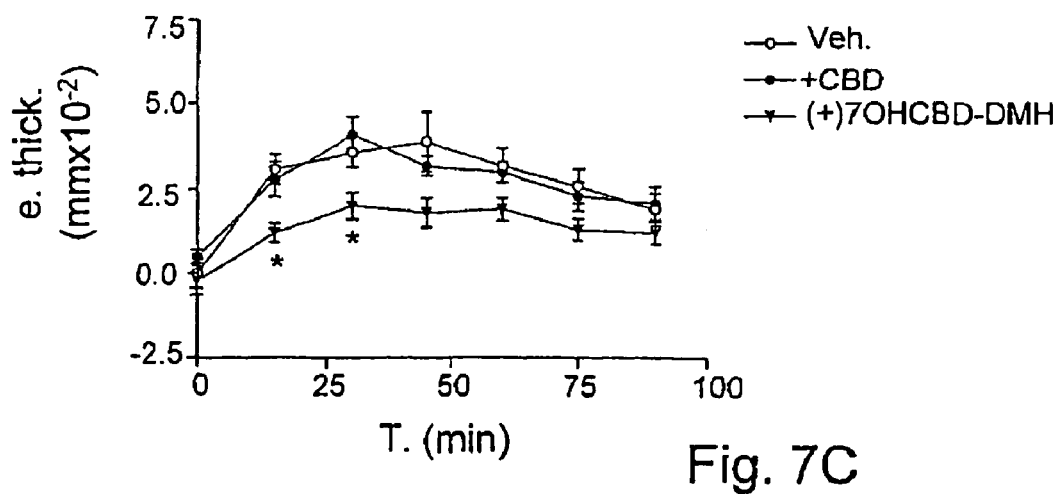

FIGS. 7A-C: Anti-inflammatory effect in a model of arachidonic acid-induced ear inflammation in the mouse.

FIG. 7A: Anti-inflammatory effect of 40 mg/kg

FIG. 7B: Anti-inflammatory effect of 10 mg/kg (+)-CBD-DMH compared to Indomethacin (20 mg/kg).

FIG. 7C: Anti-inflammatory effect of 40 mg/kg of (+)-CBD or (+)-7-OHCBD-DMH in a model of arachidonic-acid-induced ear inflammation in the mouse: Equal potencies of (+)CBD-DMH and Indomethacin.

\*) $P<0.05$ different from vehicle, or (if adjacent to vehicle-data) different from both test drugs \*\*\*) $P<0.001$ different from vehicle, or (if adjacent to vehicle-data) different from both test drugs.

Abbreviations: e. thick., ear thickness; T., time; veh., vehicle.

Figure 8:
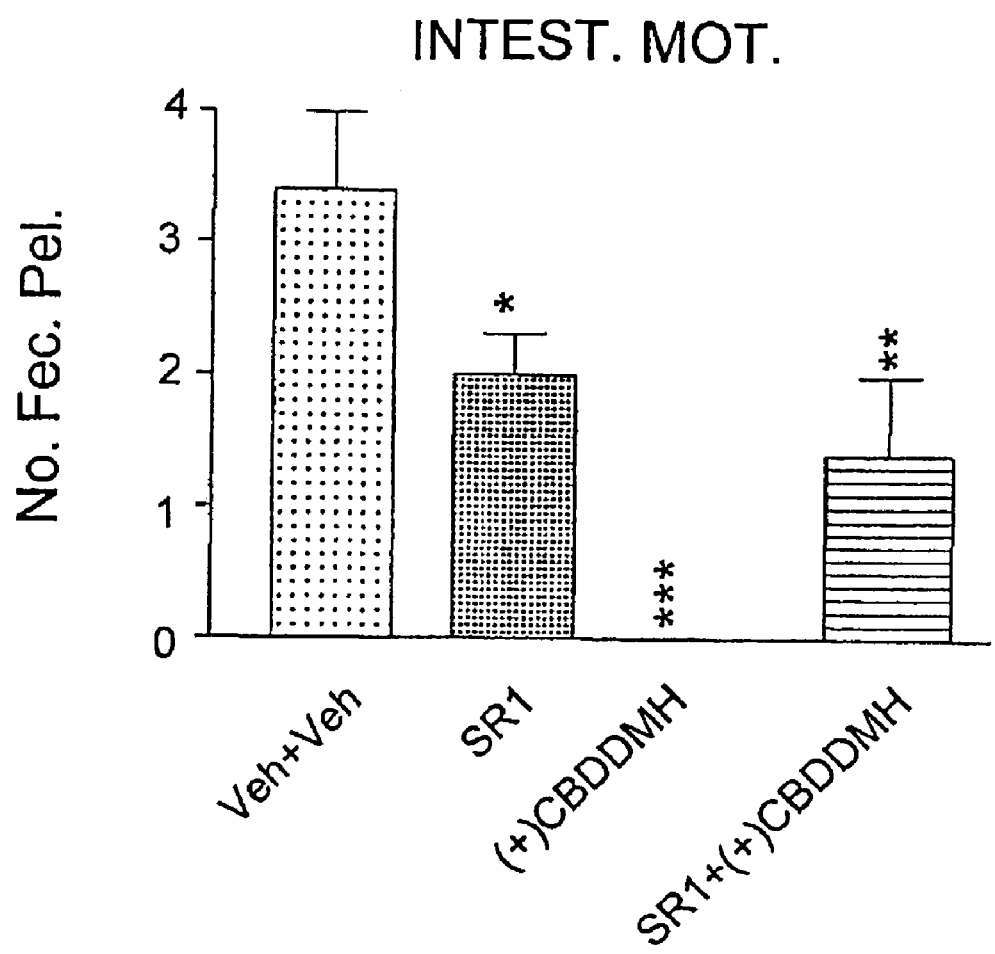

FIG. 8: Effect of compounds on intestinal motility following administration of SR1.

The figure shows partial reversal of the effect of (+)-CBD-DMH (20 mg/kg) on intestinal motility by the CBi receptor antagonist SR141716A [Sanofi] (SR1, 1 mg/kg). SR1 was injected (i.p.) 30 minutes before the agonist. 60 minutes after (+)CBD-DMH the number of fecal pellets was recorded.

\*) Different from Vehicle+Vehicle ($P<0.05$)

\*\*) Different from Vehicle+Vehicle ($P<0.01$)

\*\*\*) Different from Vehicle+Vehicle ($P<0.001$)

Abbreviations: Intest. Mot., intestinal motility; no. fec. pel., number of fecal pellets; veh., vehicle.

Figure 9:
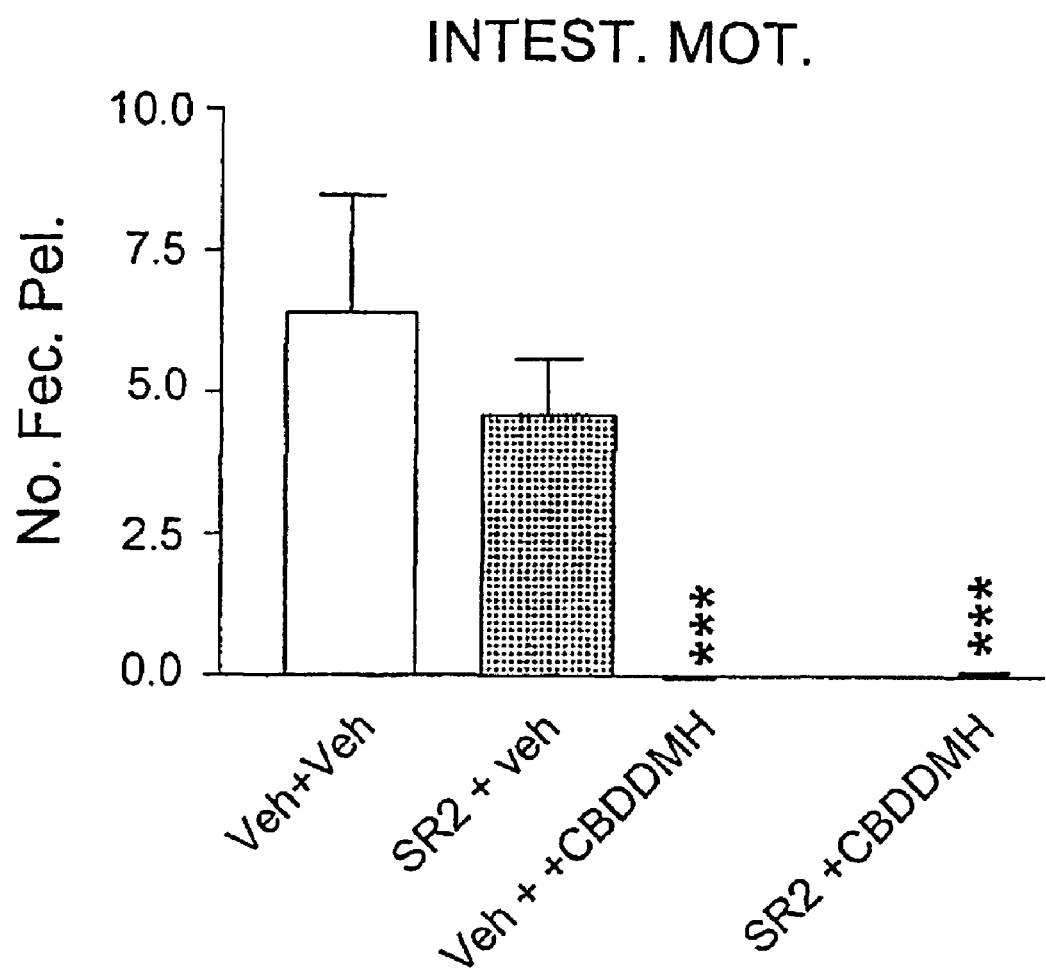

FIG. 9: Effect of compounds on intestinal motility following administration of SR2.

The figure shows that there was no reversal of the effect of (+)-CBD-DMH (20 mg/kg) on intestinal motility by the $CB_2$ receptor antagonist SR144528 [Sanofi] (SR2, 1 mg/kg). SR2 was injected (i.p.) 30 minutes before the agonist. 60 minutes after (+)-CBD-DMH the number of fecal pellets was recorded.

\*) Different from Vehicle+Vehicle ($P<0.05$)

\*\*) Different from Vehicle+Vehicle ($P<0.01$)

\*\*\*) Different from Vehicle+Vehicle ($P<0.001$)

Abbreviations: Intest. Mot., intestinal motility; no. fec. pel., number of fecal pellets; veh., vehicle.

Figure 10:
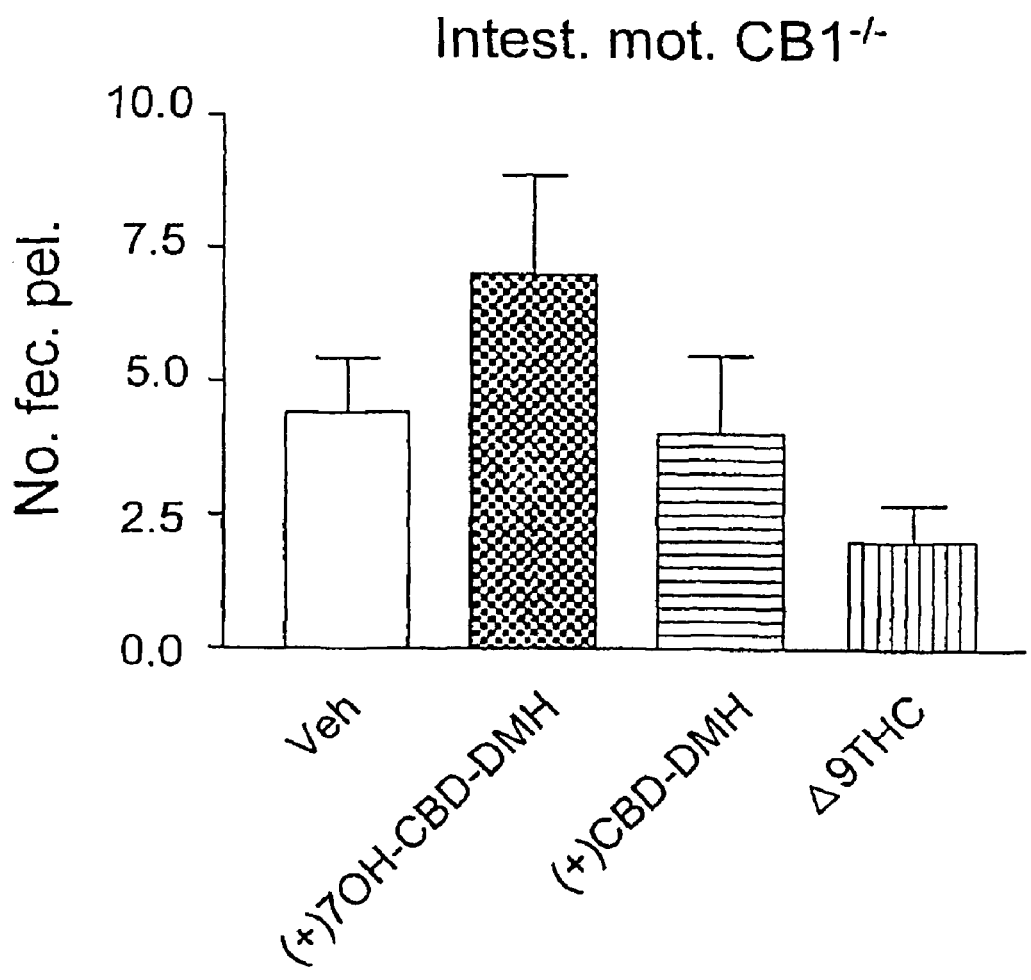

FIG. 10: Effects on intestinal motility in $CB_1-/-$ knockout mice The figure shows that there were no effects of (+)-7-OH-CBD-DMH and (+)-CBD-DMH on intestinal motility in $CB_1-/-$ knockout mice. Female $CB_1-/-$ knockout mice were injected i.p. with (+)-7-OH-CBD-DMH, (+)-CBD-DMH or $\Delta^9$-THC (20 mg/kg). Intestinal motility (defecation rate) was recorded for a period of 3 hours. No significant effects were observed for any compound.

Abbreviations: Intest. Mot., intestinal motility; no. fec. pel., number of fecal pellets; veh., vehicle.

Figure 11A:
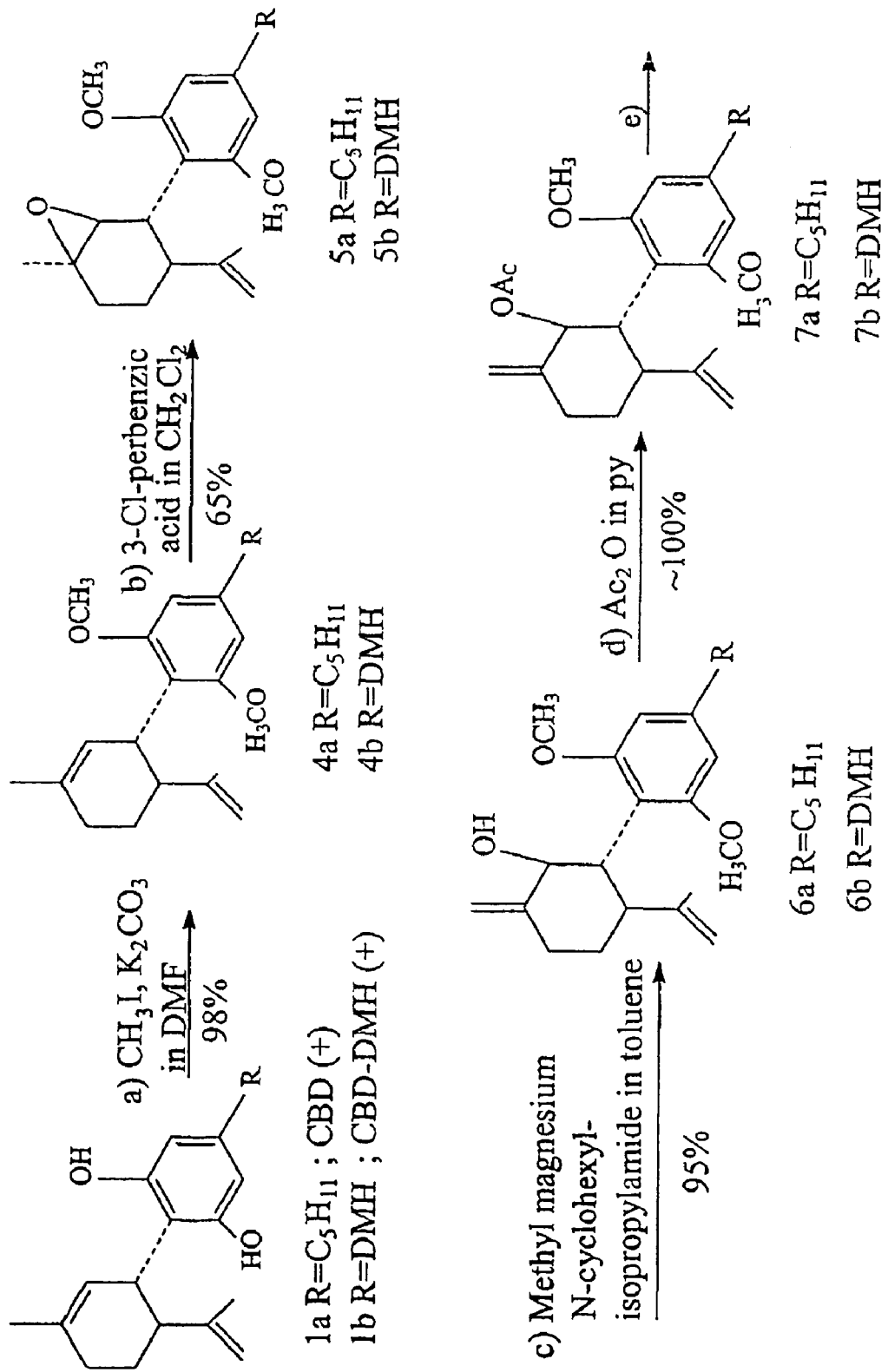
Figure 11B:
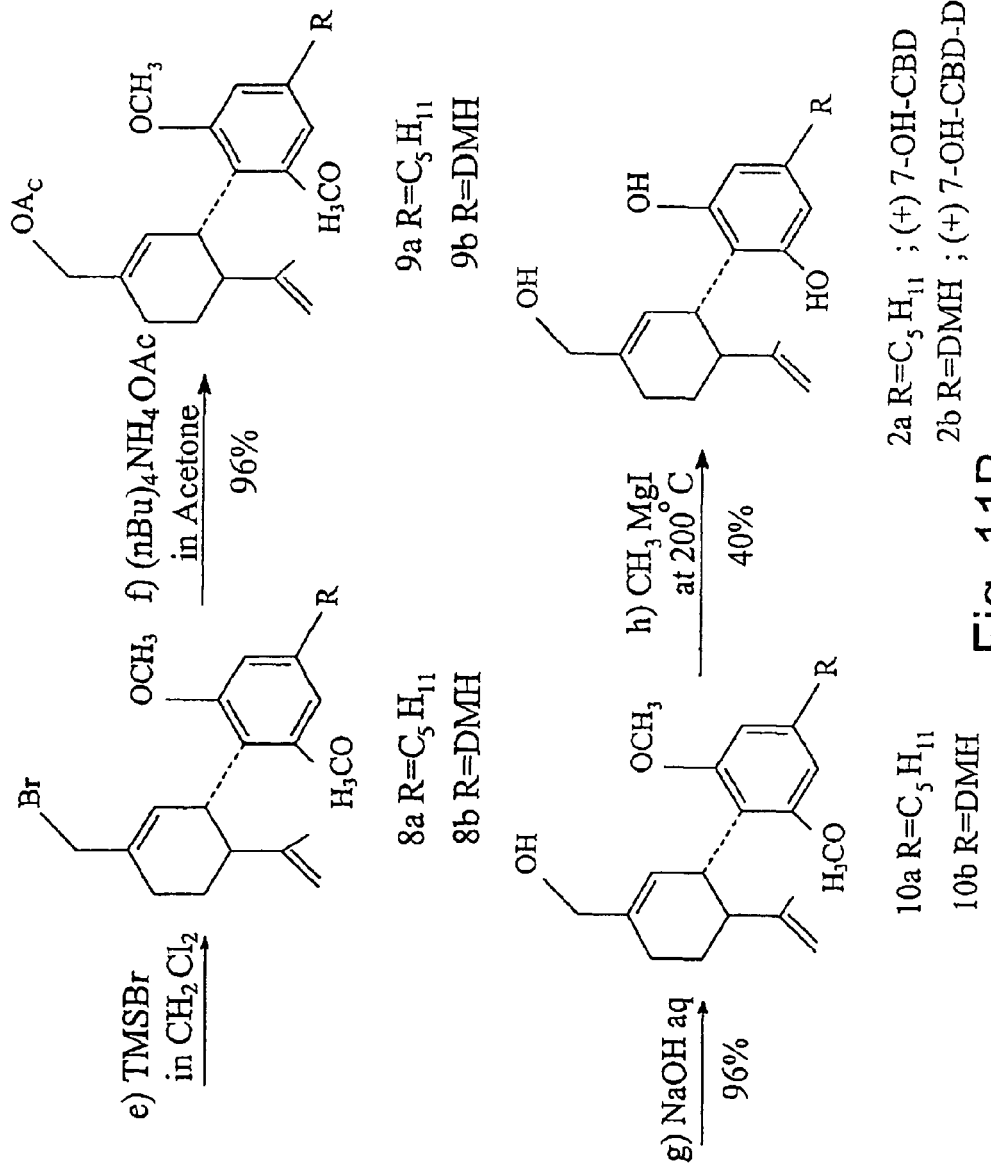
Figure 11C:
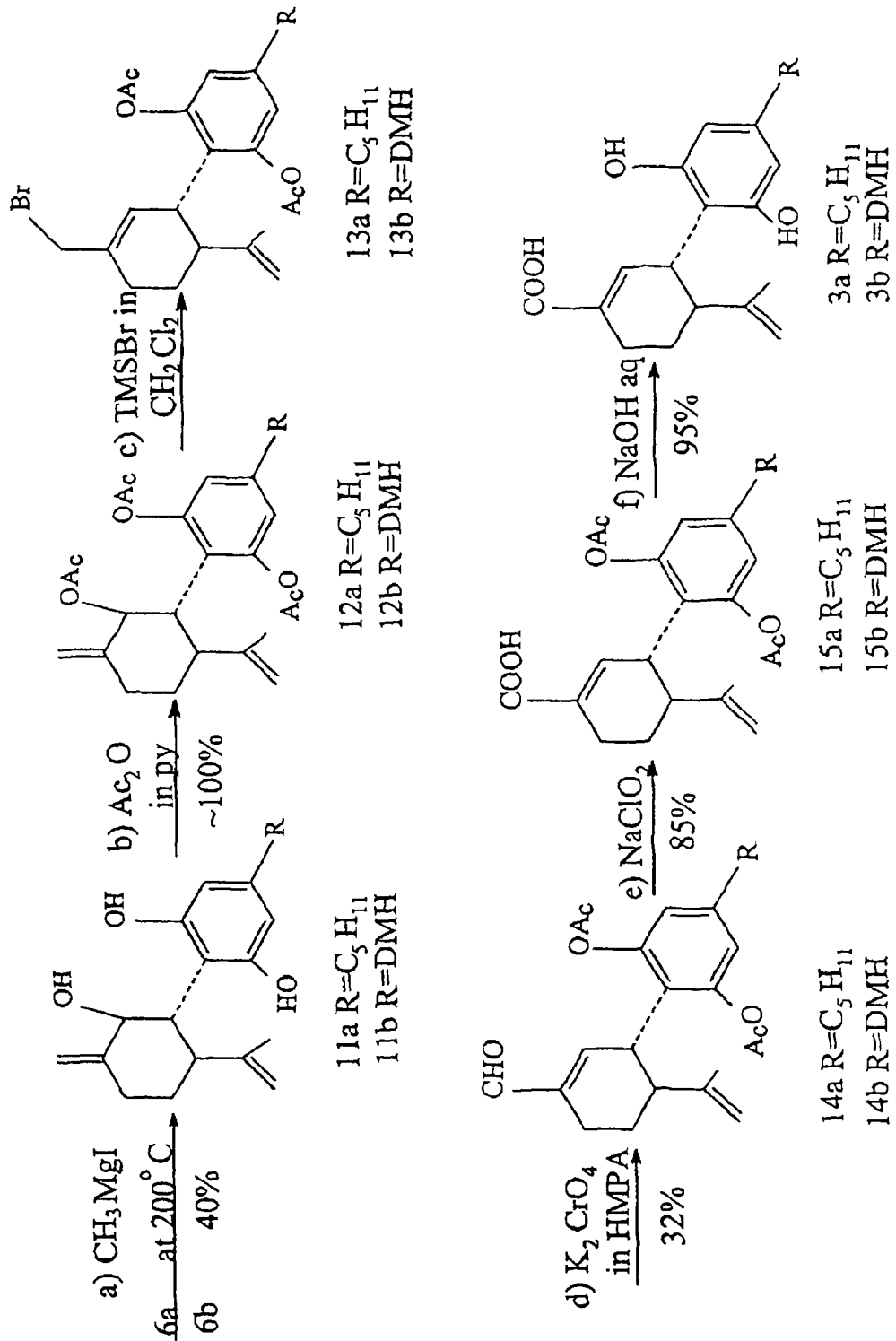

FIGS. 11A-C: Synthesis of the (+)-CBD derivatives.

FIG. 11A: Synthesis of compounds in which R' is $CH_2OH$, steps a) to d).

FIG. 11B: Continuation of FIG. 11A, synthesis of compounds in which R' is $CH_2OH$, steps e) to h).

FIG. 11C: Synthesis of compounds in which R' is COOH.

DETAILED DESCRIPTION OF THE INVENTION

In search for selective modulators of the peripheral cannabinoid system, the inventors tested a series of novel cannabidiol analogues for their in vivo central as well as peripheral activity.

Thus, the present invention relates to an optically pure (+) enantiomer of a compound of the formula:

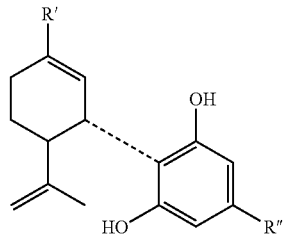

Formula I wherein:

R' designates a —COOH or —$CH_2OH$ group, and

R" designates (i) a straight or branched $C_5$-$C_{12}$ alkyl group, or (ii) an —OR'" group wherein R'" designates a straight or branched $C_5$-$C_8$ alkyl group which may be optionally substituted with a phenyl group on the terminal carbon atom, or (iii) a —$(CH_2)_n$—O—$C_{1-5}$ alkyl group, wherein n is an integer of from 1 to 7;

with the proviso that R' is not —$CH_2OH$ when R" is pentyl or dimethylheptyl, and pharmaceutically acceptable salts and esters thereof.

In preferred compounds, R' is —COOH and R" is a pentyl or dimethylheptyl group.

The invention also relates to a pharmaceutical composition containing as active ingredient a compound of formula I wherein the substituents are defined as above, and optionally further comprising at least one pharmaceutically acceptable carrier, additive, excipient or diluent. The pharmaceutical composition of the invention may optionally further comprise an additional pharmaceutically active agent.

A preferred diluent is a mixture of ethanol:cremophor:saline (1:1:18).

Central activity of the compounds of the invention was assessed in the "tetrad", which is a series of assays commonly used to measure central cannabimimmetic effects [Martin, B. R. et al. (1991) *Pharmacol. Biochem. Behav.* 40(3): 471-8; Fride, E. and C. Sanudo-Pena (2002) id. ibid.]. Three parameters for peripheral activity were used. Since gastrointestinal transit is regulated locally in the periphery rather than by centrally located $CB_1$ receptors [Izzo (2000) id. ibid.; Landi (2002) id. ibid.], intestinal motility was one of the parameters used, and peripheral cannabinoid effects was measured as rates of defecation (see Example 29). As demonstrated in the following Examples, central and peripheral effects of cannabidiol (CBD) analogues can be conveniently distinguished using this paradigm.

Thus, in a further aspect the invention relates to use of a (+) enantiomer of a compound of the formula:

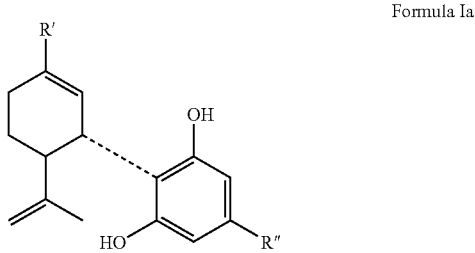

Formula Ia wherein R' designates a $CH_3$, —COOH or —$CH_2$OH group and R" designates a straight or branched $C_5$-$C_{12}$ alkyl group, an —OR' group wherein R'" designates a straight or branched $C_5$-$C_9$ alkyl group which may be optionally substituted with a phenyl group on the terminal carbon atom, or a —$(CH_2)_n$—O—$C_{1-5}$ alkyl group, wherein n is an integer of from 1 to 7, or a pharmaceutically acceptable salt or ester as a selective modulator of the peripheral cannabinoid system.

Preferably, the (+) enantiomer of a compound of formula Ia is used as an analgesic agent, a modulator of the immune system, an anti-inflammatory agent, or as a modulator of the gastrointestinal tract, particularly an anti-diarrheal agent.

The invention further relates to the use of a (+) enantiomer of a compound of the formula (Ia) wherein the substituents are as defined above or a pharmaceutically acceptable salt or ester thereof, in the preparation of a pharmaceutical composition for the selective treatment of disorders associated with the peripheral cannabinoid system.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein.

As presented in FIGS. 7A-C, in vivo inflammatory responsiveness to arachidonic acid-induced inflammation of the external ear [Young, J. M. et al. (1984) *J. Invest. Dermatol.* 82, 367-71; Hanus (1999) id. ibid.] was tested. With this method it was shown that (+) CBD-DMH is as effective as indomethacin in preventing swelling of the ear. In a separate experiment, (+)7OH-CBD-DMH also effectively prevented ear inflammation.

Thus, in particular embodiments, the pharmaceutical compositions prepared in accordance with the invention are analgesic pharmaceutical compositions, pharmaceutical compositions for the treatment of immune disorders associated with the peripheral cannabinoid system, anti-inflammatory compositions, and pharmaceutical compositions for the treatment of a disorder associated with the gastrointestinal tract, particularly anti-diarrheal pharmaceutical compositions.

The invention further relates to methods of treatment of disorders associated with the peripheral cannabinoid system by administering to a subject in need of such treatment a therapeutically effective amount of a compound of formula Ia or of a pharmaceutical composition in accordance with the invention.

As mentioned in the Background of the Invention, it was previously reported [Bisogno, T. et al. (2001) *Br. J. Pharmacol* 134, 845], that the (+)-CBD analogues have a strong affinity for the $CB_1$ receptor (e.g. (+)-7-OH-CBD-DMH, Kd=2.5+/−0.03 nM; (+)-CBD DMH, Kd=17.4+/−1.8 nM) and, more modestly, for the $CB_2$ receptor [(+)-7-OH-CBD-DMH: Kd=44 nM+/−3.1 nM; (+)-CBD-DMH: Kd=211+/−23 nM] (see also Table 1). However, significant and consistent central activity was observed only with (+)-7OH-CBD-DMH, while the other (+)-CBD derivatives exhibited spurious or no central effects at all. All compounds, however, potently inhibited defecation over a prolonged period (4 hours) without inducing hypothermia (a measurement of central nervous system activity), thus excluding a delayed psychoactive effect. Moreover, (+)-CBD-DMH was of equal potency as indomethacin in preventing arachidonic acid-induced inflammation of the external ear. Finally, this compound also completely inhibited the second phase of formalin-induced peripheral pain, while it was not active in the hot plate test, a centrally mediated pain response [Tjolsen, A. and Hole (1997) *The Pharmacology of Pain*, Springer, Heidelberg, pp. 1-20].

The inhibitory effect of both (+)-7-OH-CBD-DMH and (+)-CBD-DMH on defecation was effectively antagonized by the $CB_1$ antagonist (SR141716A), but not at all by the $CB_2$ antagonist (SR144528), suggesting that (+)-CBD-DMH partly or fully inhibited defecation via $CB_1$ receptors. This conclusion was strengthened by the absence of inhibition of intestinal motility in $CB_1$-/- receptor knockout mice.

Since it is unlikely that (+)-CBD-DMH does not cross the blood brain barrier, while its 7-OH-counterpart does, without being bound by theory, it may be suggested that (+)-CBD-DMH is devoid of central effect because it may have antagonist or partial agonist/antagonist properties in the central nervous system, while acting as an agonist in intestinal tissue and possibly other tissues, which may be in accord with other publications. For example, tissue-specific distribution of partial agonist/antagonist properties of the same compound has been thoroughly documented for benzodiazepines and muscarinic ligands [Haefely, W. et al. (1990) *Trends Pharmacol. Sci.* 11(11): 452-6; Gardner, A. L. et al. (1988) *Trends Pharmacol. Sci. Suppl.:* 40-3; Gurwitz, D. et al. (1994) *Eur. J. Pharmacol.* 267, 21].

Although (+)-7-OH-CBD-DMH and (+)-CBD-DMH bind to $CB_2$ receptors [Bisogno et al., 2001], the complete lack of antagonism by 1 or 3 mg/kg SR144528 of the effects of the (+)-CBD analogues on defecation, excludes mediation by $CB_2$ receptors. Alternative receptor mechanisms include VR1 receptors. Since the VR1 receptor antagonist capsazepine did not affect anandamide-induced intestinal immotility [Izzo, A. A. et al. (2001) *Br. J. Pharmacol.* 132, 1411], the VR1 receptor is unlikely to play such role. Further, since the CBD analogues, except (+)-CBD, did not stimulate VR1 receptors [Bisogno (2001) id. ibid.], mediation via VR1 receptors is excluded. Moreover, the inventors have shown that indeed, capsazepine did not affect the inhibition of defecation induced by (+)-CBD-DMH or (+)-7-OH-CBD-DMH (data not shown).

In conclusion, the inventors have shown that of a series of (+)-CBD analogues, all of which bind $CB_1$ and to a lesser extent $CB_2$ receptors, all except (+)-CBD itself, inhibit intestinal activity. These observations indicate that the two analogues ((+)CBD-DMH and (+)-7-OH-CBD-DMH), inhibited defecation, at least in part, via $CB_1$ receptors. Further, the inventors have shown the anti-inflammatory and analgesic capacity of these compounds in the periphery. But for (+)7-OH-CBD-DMH, none of the (+)-CBD analogues had central activity. It may be suggested that (+)-CBD-DMH, (+)-7-OH-CBD, (+)-COOH-CBD and (+)-COOH-CBD-DMH have partial agonist/antagonist effects in the central nervous system, but agonist properties in intestinal tissue. In addition, especially the acids, may not be able to cross the blood-brain barrier, thereby being prevented from exerting a central effect. Therefore these (+)-CBD analogues, via $CB_1$ receptors intestine-relaxing and anti-inflammatory/peripheral pain activities, may be developed as cannabinoid-based medicinal drugs for peripheral conditions such as inflammatory bowel disease, diarrhea and inflammatory pain.

Thus, the invention relates to use of a compounds of formula Ia, wherein the substituents are as defined above, as $CB_1$ receptor partial agonist or antagonist in the central nervous system, but CB' agonist in the peripheral system, particularly the intestines.

The invention further relates to the use of centrally inactive (+)CBD analogues as anti-diarrheal, anti-inflammatory and analgesic drugs for the gastrointestinal system and other peripheral systems.

Particularly preferred compounds are (+)-CBD-DMH, (+)-COOH-CBD and (+)-COOH-CBD-DMH.

The invention also relates to some novel (+)-CBD derivatives.

Lastly, the invention provides a method of treatment of peripheral conditions, said method comprising administering a therapeutically effective amount of the pharmaceutical composition which comprises as active ingredient the enantiomer of a compound of formula Ia to a subject in need.

The peripheral conditions to be treated by the method of the invention are inflammatory bowel disease, diarrhea and inflammatory pain.

Said therapeutic effective amount, or dosing, is dependent on severity and responsiveness of the condition to be treated, with the course of treatment lasting from several days to several months, or until a cure is effected or a diminution of the condition is achieved. In general, the medical personnel in charge of the subject in need of the treatment can easily determine optimum dosages, dosing methodologies and repetition rates.

Various methods of administration may be used for delivering the compounds of the invention or a composition thereof to a subject in need. The compounds of the invention, or compositions thereof, may be delivered via intravenous (i.v.), intramuscular (i.m.) intraperitoneal (i.p.) injections, orally (in liquid form or prepared as dosage unit forms like capsules, tablets, granules, pills, lozenges, etc.).

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Materials Amid Methods

Mice

Female Sabra mice (2-3 months of age) were purchased from Harlan, Israel. Breeding pairs of $CB_1$–/– receptor knockout mice were provided by Prof. A. Zimmer, University Clinic Bonn, Germany.

Drugs

All (cannabidiol-derived) compounds were prepared in the inventors' laboratory (Department of Medicinal Chemistry and Natural Products, Hebrew University of Jerusalem). The $CB_1$ and $CB_2$ receptor antagonists, SR141716A and SR144528, respectively, were kindly supplied by NIDA (Research Triangle). All compounds were prepared in a mixture of ethanol:cremophor (Sigma):saline=1:1:18 (see for example [Fride, E. and R. Mechoulam (1993) id. ibid.].

The synthesis of the (+)-CBD derivatives is schematically illustrated in FIGS. 11A, 11B and 11C and in the following Examples.

In the following synthesis Examples the numbers of compounds in brackets are as indicated in FIGS. 11A, 11B and 11C.

Synthesis of compounds in which R" is —O—R'" is performed according to Johnson and Melvin [Johnson and Melvin (1986) id ibid.].

Example 1

(+)-Dimethoxy-CBD (4a)

(+)-CBD (1a), (3 g, 9.95 mmol) was dissolved in DMF (55 ml). $K_2CO_3$ (7.35 g, 53.3 mmol) and $CH_3I$ (2.3 ml, 36.9 mmol) were added and the mixture was stirred at room temperature for 4 hours. The reaction was monitored by TLC (10% ether/P. E.) till the starting material disappeared. Then, 200 ml of water were added and the solution extracted with ether. The organic phase was washed with brine till neutral pH, dried on $MgSO_4$ and filtered. Removal of the solvent under reduced pressure afforded 3.2 g of the product (yield 98%).

(4a): $^1$H-NMR δ 6.344 (2H, s, Ar), 5.220 (1H, s, olefin), 4.460-4.436 (2H, d, J=7.2 Hz), 4.023-3.971 (1H, m, benzyl), 3.741 (6H, s, $OCH_3$), 2.960-2.869 (1H, td, J=11.5, 4.5 Hz, allyl), 2.717-2.569 (2H, t, J=7.5 Hz, benzyl), 2.259-2.144 (1H, m), 2.018-1.960 (1H, m), 1.789-1.722 (1H, m), 1.678

(3H, s, allyl CH$_3$), 1.568 (6H, br s), 1.352 (4H, m) 0.936-0.890 (3H, t, J=6.8 Hz, terminal CH$_3$).

IR: 2875, 1600, 1570, 1440, 1410, 1220, 1100, 880 cm$^{-1}$.

[α]$_D$: +96.8° (c 12.19 mg/ml, CHCl$_3$)

Example 2

(+)-Dimethoxy-CBD-DMH (41b)

Prepared with the same procedure reported for (4a), with (+)-CBD-DMH as starting material.

(41b): $^1$H-NMR δ 6.449 (2H, s, Ar), 5.238 (1H, s, olefin), 4.422-4.382 (2H, d, J=12.0 Hz), 4.120-3.901 (1H, m, benzyl), 3.784 (6H, s, OCH$_3$), 2.933-2.801 (1H, m, benzyl), 2.270-2.086 (1H, m, allyl), 2.048-1.924 (1H, m), 1.781-1.501 (10H, m), 1.253-1.185 (10H, m), 1.105-0.962 (2H, m) 0.849-0.8816 (3H, t, J=6.8 Hz, terminal CH$_3$).

IR: 2900, 1600, 15780, 1440, 1400, 1100 cm$^{-1}$.

[α]$_D$: +98.1° (c 2.04 mg/ml, CHCl$_3$)

Example 3

(+)-1,2 Oxido-dimethoxy-hexahydrocannabinol (5a)

3-Chloro-perbenzoic acid (70% pure 1.2 g, 4.85 mmol) was dissolved in 50 ml CH$_2$Cl$_2$ and the solution was cooled to 0° C. A solution of (4a) (1.65 g, 4.82 mmol) in 10 ml CH$_2$Cl$_2$ was slowly injected. The reaction mixture was stirred at 0° C. for 30 minutes and monitored by TLC (10% Ether/P. E.). The reaction was quenched by addition of a saturated aqueous solution of NaHCO$_3$ and the organic phase was separated by a separatory funnel, then the aqueous phase was extracted with ether. The combined organic extracts were washed with brine, dried over MgSO$_4$ and filtered. Removal of the solvents under reduced pressure afforded a residue that was flash chromatographed (7% Ether/P. E) to give the epoxy-derivative (5a) (yield 65%).

(5a): $^1$H-NMR δ 6.348-6.322 (2H, d, J=7.7 Hz, Ar), 4.369 (1H, s, olefin), 4.159 (1H, s, olefin), 3.803 (3H, s, OCH3), 3.714 (3H, s, OCH$_3$), 3.612-3.571 (1H, d, J=12.2, Hz, H on epoxide ring), 2.574-2.522 (2H, t, J=7.9 Hz, benzyl), 2.293-2.201 (1H, m), 2.081-1.995 (1H, m), 1.882-1.757 (1H, m), 1.628-1.585 (6H, m), 1.364-1.313 (9H, m), 0.936-0.890 (3H, t, J=6.5 Hz, terminal CH3).

IR: 2900, 1610, 1580, 1460, 1420, 1120, 760 cm$^{-1}$.

Example 4

(+)-1,2 Oxidodimethoxyhexahydrocannabinol DMH (5b)

Prepared with the same procedure reported for (5a), but the yield was slightly better (70%).

(5b): $^1$H-NMR δ 6.466-6.442 (2H, d, J=7.2 Hz, Ar), 4.358 (1H, s, olefin), 4.121 (1H, s, olefin), 3.805 (3H, s, OCH$_3$), 3.719 (3H, s, OCH$_3$), 3.591-3.555 (1H, d, J=10.8, Hz, H on epoxide ring), 2.235-2.193 (1H, m, benzyl), 2.105-1.995 (1H, m, allyl), 1.907-1.761 (1H, m), 1.745-1.514 (10H, m), 1.369 (3H, s, allyl CH$_3$), 1.268-1.180 (10H, m), 1.081-0.942 (2H, m.), 0.856-0.812 (3H, t, J=6.5 Hz, terminal CH$_3$).

IR: 2900, 1600, 1580, 1460, 1450, 1210, 1110, 750 cm$^{-1}$.

Example 5

(3S,4S)-3-[2,6-Dimethoxy-4-pentylphenyl]-2-hydroxy-4-isopropenyl-1-methylene cyclohexane (6a)

Butyllithium in hexane (5.6 ml, 14 mmol) was added to a 0° C. solution of N-cyclohexylisopropylamine (1.85 ml, 11.3 mmol) in anhydrous toluene (10 ml, distilled over sodium) under N$_2$ atmosphere. After 15 minutes, methylmagnesium bromide in ether (3.8 ml, 11.4 mmol) was injected, and the reaction mixture was stirred for 45 minutes at room temperature. A solution of (5a) (1 g, 2.79 mmol) in dry toluene (3 ml) was added, and the mixture was heated to 40° C. and stirred for two hours. Then the reaction was cooled to 0° C. and quenched by the slow addition of 5M HCl. The organic phase was separated by a separatory funnel, and then the aqueous phase was extracted with ether. The combined organic extracts were washed with brine, dried over MgSO$_4$ and filtered. Removal of the solvents under reduced pressure afforded a residue that on TLC (20% Ether/P. E.) showed only one spot, and by $^1$H-NMR was proved to be (6a) (yield 97%).

(6a): $^1$H-NMR δ 6.332 (2H, s, Ar), 5.083 (1H, s, olefin), 4.821 (1H, s, olefin), 4.662-4.622 (1H, d, J=11.8 Hz, CHOH), 4.387 (1H, s, olefin), 4.379 (1H, s, olefin), 3.798 (3H, s, OCH$_3$), 3.745 (3H, s, OCH$_3$), 3.200-3.154 (1H, td, J=11.2, 3.0 Hz, benzyl), 2.564-2.452 (3H, m), 2.255-1.625 (1H, m), 1.754-1.707 (1H, m), 1.609-1.350 (4H, m), 1.432 (3H, s, allyl CH$_3$), 1.350-1.313 (4H, m), 0.924-0.878 (3H, t, J=6.5 Hz, terminal CH$_3$).

IR: 3400, 2920, 1590, 1450, 1120, 900, 730 cm$^{-1}$.

[α]$_D$: −62.3° (c 15.36 mg/ml, CHCl$_3$)

Example 6

(3S,4S)-3-[4-(1',1'-Dimethylheptyl)-2,6-dimethoxyphenyl]-2-hydroxy-4-isopropenyl-1-methylenecyclohexane (6b)

Prepared with the same procedure reported for (6a).

(6b): $^1$H-NMR δ 6.440 (2H, s, Ar), 5.080 (1H, s, olefin), 4.821 (1H, s, olefin), 4.655-4.621 (1H, d, J=9.0 Hz, CHOH), 4.448 (1H, s, olefin), 4.338 (1H, s, olefin) 3.802 (3H, s, OCH$_3$), 3.744 (3H, s, OCH$_3$), 3.215-3.127 (1H, td, J=11.7, 3.0 Hz, benzyl), 2.505-2.444 (1H, dt, J=12.6, 3.0 Hz allyl), 2.255-2.182 (1H, td, J=9.0, 3.0 Hz), 1.740-1.688 (2H, m), 1.555-1.423 (8H, m), 1.301-1.177 (10H, m), 1.025-0.955 (2H, m), 0.859-0.814 (3H, t, J=6.5 Hz, terminal CH$_3$).

IR: 3400, 2900, 1600, 1560, 1450, 1400, 1110, 750 cm$^{-1}$.

[α]$_D$: −47.6° (c 1.05 mg/ml, CHCl$_3$)

Example 7

(3S,4s)-3-[2,6-Dimethoxy-4-pentylphenyl]-2-acetoxy-4 isopropenyl-1-methylene-cyclohexane (7a)

(6a) (0.9 g, 2.5 mmol) was dissolved in pyridine (py) (2 ml) and acetic anhydride (2 ml) and the reaction was stirred for 18 hours at room temperature. Then the solution was poured onto ice water (20 ml) and extracted with ether. The combined organic extracts were washed successively with 1 N HCl, aqueous sodium bicarbonate and brine, dried on MgSO$_4$ and filtered. Removal of the solvents under reduced pressure afforded an oily residue that on TLC (20% Ether/P. E.) showed only one spot, that by $^1$H-NMR was proved to be (7a) (yield ~100%).

(7a): $^1$H-NMR δ 6.281-6.267 (2H, d, J=4.2 Hz, Ar), 5.967-5.931 (1H, d, J=10.8 Hz, olefin), 4.767-4.721 (2H, d, J=13.7

Hz, olefin), 4.535 (1H, s, olefin), 4.419 (1H, s, olefin), 3.793 (3H, s, OCH$_3$), 3.745 (3H, s, OCH$_3$), 3.491-3.416 (1H, t, J=11.4 Hz), 3.286-3.197 (1H, td, J=11.4, 2.7, Hz, benzyl), 2.533-2.469 (2H, t, J=7.2 Hz), 2.325-2.249 (1H, m), 1.717 (3H, s, OAc), 1.625-1.447 (6H, m), 1.404-1.250 (6H, m), 0.924-0.878 (3H, t, J=6.5 Hz, terminal CH$_3$).

IR: 2910, 1750, 1450, 1360, 1240, 1120, 890 cm$^{-1}$.

Example 8

(3R,4R)-3-[4-(1',1'-Dimethylheptyl)-2,6-dimethoxyphenyl]-2 acetoxy-1-methylene-cyclohexane (7b)

Prepared with the same procedure reported for (7a).

(7b): $^1$H-NMR δ 6.409-6.377 (2H, d, J=8.1 Hz, Ar), 5.980-5.931 (1H, d, J=14.5 Hz, CHOAc), 4.768-4.717 (2H, d, J=15.2 Hz, olefin), 4.521 (1H, s, olefin), 4.405 (1H, s, olefin), 3.802 (3H, s, OCH$_3$), 3.754 (3H, s, OCH$_3$), 3.268-3.181 (1H, m, benzyl), 2.522-2.459 (1H, m, allyl), 1.781-1.717 (1H, m), 1.695 (3H, s, OAc), 1.540-1.484 (6H, m), 1.239-1.171 (14H, m), 0.980-0.923 (2H, m), 0.854-0.809 (3H, t, J=6.7 Hz, terminal CH$_3$).

IR: 290, 1750, 1450, 1360, 1240, 1120, 880 cm$^{-1}$.

Example 9

(+)-7-Bromo-dimethoxy CBD (8a)

(7a) (1 g, 2.5 mmol) was dissolved in dry CH$_2$Cl$_2$ (50 ml, distilled over CaH$_2$) under nitrogen atmosphere and TMSBr (Bromotrimethylsilane) (1.6 ml, 12.1 mmol) was added. The reaction was stirred at room temperature for 4 hours, then it was shaken with a saturated aqueous solution of NaHCO$_3$ and the organic phase was separated by a separatory funnel, then the aqueous phase was extracted with ether. The combine organic extracts were washed with brine, dried over MgSO$_4$ and filtered. Removal of the solvents afforded a residue that H-NMR and TLC (20% Ether/P. E.) showed predominantly a single component, which was used immediately with no purification.

(8a): δ 6.322 (2H, s, Ar), 5.736 (1H, s, olefin), 4.767 (1H, s, olefin), 4.454), 4.535 (1H, s, olefin), 4.006 (2H, s, CH$_2$Br), 3.736 (6H, s, OCH$_3$), 2.853-2.767 (1H, td, J=11.9, 3.2 Hz, benzyl), 2.565-2.512 (1H, t, J=7.9, Hz, benzyl), 2.397-2.359 (1H, m), 2.277-2.183 (1H, m), 1.870-1.662 (2H, m), 1.619 (3H, s, allyl CH$_3$), 1.439-1.237 (7H, m), 0.928-0.882 (3H, t, J=6.6 Hz, terminal CH$_3$).

IR: 2900, 1580, 1460, 1230, 1120 cm$^{-1}$.

Example 10

(+)-7-Bromo-dimethoxy CBD DMH (8b)

Prepared with the same procedure reported for (8a).

(8b): $^1$H-NMR δ 6.431 (2H, s, Ar), 5.602 (1H, s, olefin), 4.821-4.337 (4H, m, CH$_2$Br+olefin), 4.042-3.961 (1H, m, olefin), 3.720 (6H, s, OCH$_s$), 3.116-3.010 (1H, m, benzyl), 2.842-2.762 (1H, allyl), 1.782-1.517 (9H, m), 1.247-1.178 (10H, m), 1.010 (2H, br s), 0.831 (3H, br s, terminal CH$_3$).

IR: 2910, 1580, 1460, 1230, 1120 cm$^{-1}$.

Example 11

(+)-7-Acetoxy-dimethoxy CBD (9a)

(8a) (570 mg, 1.35 mmol) was dissolved in acetone (15 mol, stored on 4A° molecular sieves) and tetrabutylammonium acetate ((nBu)$_4$NH$_4$OAc) (450 mg, 1.49 mmol). The mixture was stirred, refluxed and monitored by TLC (20% Ether/P. E.). After 2 hours there was no more starting material. The acetone was removed under reduced pressure, and the residue was diluted with water (20 ml) and extracted with ether. The combine organic extracts were washed with aqueous sodium bicarbonate and brine, dried on MgSO$_4$ and filtered. Removal of the solvents under reduced pressure afforded 520 mg of an oily residue (96% yield).

(9a): $^1$H-NMR δ 6.320 (2H, s, Ar), 5.581 (1H, s, olefin), 4.492-4.386 (4H, m, CH$_2$OAc+olefin), 4.040-3.986 (1H, m, benzyl), 3.715 (6H, s, OCH$_3$), 2.853-2.801 (1H, m), 2.195-2.071 (2H, m), 2.060 (3H, s, OAc), 1.823-1.695 (2H, m), 1.605 (5H, br s), 1.323 (4H, br s), 0.921-0.875 (3H, t, J=6.7 Hz, terminal CH$_3$).

IR: 2900, 1720, 1580, 1440, 1110 cm$^{-1}$.

[α]$_D$: +135.2° (c 15.95 mg/ml, CHCl$_3$)

Example 12

(+)-7-Acetoxy-dimethoxy CBD DMH (9b)

Prepared with the same procedure reported for (9a), but the yield was slightly worse (90%).

(9b): $^1$H-NMR δ 6.440 (2H, s, Ar), 5.609 (1H, s, olefin), 4.498-4.343 (4H, m, CH$_2$OAc+olefin), 4.041-3.965 (1H, m, benzyl), 3.719 (6H, s, OCH$_s$), 2.845-2.763 (1H, m, allyl), 2.193-2.099 (2H, m), 2.061 (3H, s, OAc), 1.796-1.776 (2H, m), 1.594-1.518 (7H, m), 1.254-1.179 (10H, m), 1.015 (2H, brs), 0.856-0.861 (3H, t, J=6.4 Hz, terminal CH$_3$).

IR: 2900, 1720, 1600, 1580, 1450, 1410, 1220 cm$^{-1}$.

[α]$_D$: +90.5 (c 2.53 mg/ml, CHCl$_3$)

Example 13

(+)-7-Hydroxy-dimethoxy CBD (10a)

(9a) (500 mg, 1.25 mmol) was dissolved in ethanol (20 ml) and NaOH 1N (2 ml) was added and the reaction was refluxed for 1 hour. The ethanol was removed under reduced pressure, and the residue was diluted with water (20 ml) and HCl 2N was added till acid pH. The solution was extracted with ether. The combined organic extracts were washed brine, dried on MgSO$_4$ and filtered. Removal of the solvents under reduced pressure afforded 430 mg of an oily residue (96% yield).

(10a): $^1$H-NMR δ 6.328 (2H, s, Ar), 5.510 (1H, s, olefin), 4.458-4.414 (2H, d, J=13.2 Hz, olefin), 4.010 (2H, br s, CH$_2$OH), 3.728 (6H, s, OCH$_3$), 2.858-2.806 (1H, m, benzyl), 2.566-2.508 (2H, t, J=7.5 Hz, benzyl), 2.213 (2H, m), 1.817-1.582 (7H, m), 1.451-1.259 (5H, m), 0.924-0.878 (3H, t, J=6.5 Hz, terminal CH$_3$).

IR: 3300, 2900, 1580, 1440, 1220, 1110 cm$^{-1}$.

MS m/z (relative intensity): 358 (M$^+$, 7), 327 (52), 290 (80), 221 (100), 152 (33).

Exact mass calculated for C25H3803: 358.25080, found 358.2511.

Example 14

(+)-7-Hydroxy-dimethoxy CBD (10b)

Prepared with the same procedure reported for (10a).

(10b): $^1$H-NMR δ 6.446 (2H, s, Ar), 5.528 (1H, s, olefin), 4.434-4.367 (2H, d, J=20.1 Hz, olefin), 4.010 (3H, br s, CH$_2$OH+OH), 3.729 (6H, s, OCH$_3$), 2.905-2.785 (1H, m, benzyl), 2.248-2.105 (2H, m), 1.759-1.704 (2H, m), 1.535

(3H, s, allyl CH$_3$), 1.495-1.460 (4H, m) 1.360-1.120 (10H, m) 0.980-0.9875 (2H, m), 0.797-0.752 (3H, t, J=6.5 Hz, terminal CH$_3$).

IR: 3300, 2900, 1600, 1570, 1420, 1400, 1230, 1110, 750 cm$^{-1}$.

[α]$_D$: +135.2° (c 15.95 mg/ml, CHCl$_3$)

MS m/z (relative intensity): 414 (M$^+$, 14), 396 (8), 383 (100), 346 (43), 277 (50), 119 (7).

Exact mass calculated for C$_{27}$H$_{42}$O$_3$: 358.31340, found 358.3136.

Example 15

(+)-7-Hydroxy CBD (2a)

A Grignard reagent was prepared with magnesium (100 mg, 4.17 mmol) and CH$_3$I (0.26 ml, 4.17 mmol) in dry ether (3 ml, distilled over sodium) under N2 atmosphere. (10a) (420 mg, 1.17 mmol) in ether (1 ml) was slowly added to the stirred solution and the ether was distilled off. The residue was heated under N$_2$ atmosphere till 210° C. for 45 minutes. Then the flask was cooled to room temperature and the reaction was quenched with ice water. The aqueous solution was extracted with ether several times. The combine organic extracts were dried on MgSO$_4$ and filtered. Removal of the solvents under reduced pressure afforded a residue that was chromatographed on silica gel (25% Ether/P. E.) to give 150 mg of the pure (2a) (yield 40%).

(2a): $^1$H-NMR δ 6.200 (2H, s, Ar), 5.822 (1H, s, olefin), 4.629 (1H, s, olefin), 4.518 (1H, s, olefin), 4.075 (2H, s, CH$_2$OH), 3.962-3.923 (1H, m, benzyl), 2.567-2.484 (1H, td, J=13.3, 2.7 Hz, allyl), 2.435-2.384 (2H, t, J=7.5 Hz, benzyl), 1.882-1.734 (2H, m), 1.660 (6H, s. allyl CH$_3$), 1.584-1.487 (2H, m), 1.285-1.248 (6H, m), 0.886-0.843 (3H, t, J=6.3 Hz, terminal CH$_3$).

IR: 3300, 2900, 1620, 1580, 1440, 1240, 1020, 730 cm$^{-1}$.

[α]$_D$: +67.3° (c 19.51 mg/ml, CHCl$_3$)

MS m/z (relative intensity): 330 (M$^+$, 10), 312 (44), 299 (53), 284 (44), 244 (100), 231 (56), 187 (29), 147 (13).

Exact mass calculated for C21H3003: 330.21949, found 330.2231.

Example 16

(+)-7-Hydroxy CBD-DMH (2b)

Prepared with the same procedure reported for (2a).

(2b): $^1$H-NMR δ 6.335 (2H, s, Ar), 5.863 (1H, s, olefin), 4.652 (1H, s, olefin), 4.538 (1H, s, olefin), 4.108 (2H, s, CH$_2$OH), 3.920-3.889 (1H, d, J=9.3 Hz, benzyl), 2.498-2.433 (1H, m, allyl), 2.228 (2H, br s), 2.064-1.715 (2H, m), 1.648-1.428 (7H, m), 1.312-1.168 (12H, m), 0.853-0.808 (3H, t, J=6.5 Hz, terminal CH$_3$).

IR: 3300, 2900, 1620, 1580, 1420, 1210, 1020, 750 cm$^{-1}$.

[α]$_D$: +61.1° (c 1.8 mg/ml, CHCl$_3$)

MS m/z (relative intensity): 386 (M$^+$, 24), 369 (30), 368 (30), 355 (100), 300 (43), 287 (510), 283 (34), 249 (38), 233 (22), 187 (10).

Exact mass calculated for C$_{25}$H$_{38}$O$_3$: 386.28210, found 386.2825.

Example 17

(3S,4S)-3-[2,6-Dihydroxy-4-pentylphenyl]-2-hydroxy-4-isopropenyl-1-methylene cyclohexane (11a)

A Grignard reagent was prepared with magnesium (84 mg, 3.5 mmol) and CH$_3$I (0.2 ml, 3.5 mmol) in dry ether (1 ml, distilled over sodium) under N$_2$ atmosphere. (6a) (360 mg, 1 mmol) in ether (0.5 ml) was added to the stirred solution and the ether was distilled. The residue was heated under N$_2$ atmosphere till 210° C. for 45 minutes.

Then the flask was cooled till room temperature and the reaction was quenched with ice water. The aqueous solution was extracted several times with ether. The combined organic extracts were dried on MgSO$_4$ and filtered. Removal of the solvents under reduced pressure afforded a residue that was chromatographed on silica gel (25% Ether/P. E.) to give 132 mg of the pure (11a) (yield 40%).

(11a): $^1$H-NMR δ 6.156-6.097 (2H, d, J=17.7 Hz, Ar), 5.612 (1H, s, OH), 5.370 (1H, s, OH), 5.092 (1H, s, olefin), 4.847 (1H, s, olefin), 4.684-4.625 (2H, m, CHOH+olefin), 4.462 (1H, s, olefin), 3.300-3.205 (1H, td, J=12.7, 2.7 Hz, benzyl), 3.128-3.058 (1H, t, J=10.5, Hz, allyl), 2.270-2.141 (1H, m), 2.122-2.049 (1H, br s, OH), 1.767-1.712 (1H, m), 1.534-1.48 (5H, m), 1.290-1.183 (4H, m), 0.895-0.881 (3H, t, J=6.6 Hz, terminal CH$_3$).

IR: 3350, 2900, 1620, 1580, 1420, 1160, 1000, 750 cm$^{-1}$.

Example 18

(3S,4S)-3-[4-(1',1'-Dimethylheptyl)-2,6-dihydroxyphenyl]-2-hydroxy-4-isopropenyl-1-methylenecyclohexane (11b)

Prepared with the same procedure reported for (11a), but the yield was slightly better (45%).

(11b): $^1$H-NMR δ 6.295 (1H, s. Ar), 6.229 (1H, s, Ar), 5.786 (1H, s, OH), 5.546 (1H, s, OH), 5.127 (1H, s, olefin), 4.861 (1H, s, olefin), 4.751-4.716 (1H, d, J=3.3 Hz, CHOH), 5.127 (1H, s, olefin), 4.444 (1H, s, olefin), 3.421-3.276 (1H, m, benzyl), 3.132-3.062 (1H, t, J=10.5, Hz, allyl), 2.502-2.459 (1H, d, J=12.9 Hz), 2.251-2.175 (2H, m), 1.780-1.739 (1H, m), 1.528 (3H, s, allyl CH$_3$) 1.460-1.433 (4H, m), 1.251-1.170 (10H, m), 0.954 (2H, br s) 0.845 (3H, br s, terminal CH$_3$).

IR: 3300, 2900, 1620, 1580, 1410, 1210, 750 cm$^{-1}$.

[α]$_D$: −47.3° (c 1.48 mg/ml, CHCl$_3$)

Example 19

(3S,4S)-3-[2,6-Diacetoxy-4-pentylphenyl]-2-acetoxy-4-isopropenyl-1-methylene-cyclohexane (12a)

(11a) (100 mg, 0.3 mmol) was dissolved in pyridine (0.5 ml) and acetic anhydride (0.5 ml) and the reaction was stirred for 18 hours at room temperature. Then the solution was poured onto iced water (10 ml) and extracted with ether. The combine organic extracts were washed successively with 1 N HCl, aqueous sodium bicarbonate and brine, dried on MgSO$_4$ and filtered. Removal of the solvents under reduced pressure afforded 136 mg of an oily residue that by NMR was proved to be (12a) (yield ~100%).

(12a): $^1$H-NMR δ 6.861 (1H, s, Ar), 6.696 (1H, s, Ar), 5.725-5.688 (1H, d, J=11.1 Hz, CHOAC), 4.083 (1H, s, olefin), 4.689 (1H, s, olefin), 4.540-4.515 (2H, d, J=7.5 Hz, olefin), 3.180-3.105 (1H, t, J=11.3 Hz, benzyl), 2.893-2.802 (1H, td, J=11.3, 3.2 Hz, allyl), 2.563-2.513 (2H, t, J=7.5, Hz, benzyl), 2.374 (3H, s, OAc), 2.280 (3H, s, OAc), 1.798 (3H, s, OAc), 1.614-1.470 (5H, m), 1.286-1.246 (8H, m), 0.886-0.844 (3H, t, J=6.3 Hz, terminal $CH_3$).

IR: 2910, 1750, 1410, 1350, 1180, 1130, 890 $cm^{-1}$.

Example 20

(3S,4S)-3-[2,6-Diacetoxy-4-(1',1'-dimethylheptyl)-phenyl]-2-acetoxy-4-isopropenyl-1-methylenecyclohexane (12b)

Prepared with the same procedure reported for (12a).

(12b): $^1$H-NMR δ 6.947 (1H, s, Ar), 6.795 (1H, s, Ar), 5.732-5.695 (1H, d, J=11.0 Hz, CHOAC), 4.798 (1H, s, olefin), 4.691 (1H, s, olefin), 4.540-4.515 (2H, d, J=7.5 Hz, olefin), 3.167-3.095 (1H, t, J=11.3 Hz, benzyl), 2.854-2.816 (1H, m, allyl), 2.561-2.515 (1H, d, J=13.8, Hz, benzyl), 2.372 (3H, s, OAc), 2.287 (3H, s, OAc), 2.230-2.195 (1H, m), 1.825-1.770 (4H, m), 1.538-1.424 (6H, m), 1.224-1.151 (12H, m), 0.955-0.945 (2H, m) 0.840-0.799 (3H, t, J=6.1 Hz, terminal $CH_3$).

IR: 2900, 1750, 1410, 1360, 1180, 1130, 890 $cm^{-1}$.

Example 21

(+)-7-Bromo-diacetate CBD (13a)

(12a) (100 mg, 0.2 mmol) was dissolved in dry $CH_2Cl_2$ (10 ml, distilled over CaH2) under nitrogen atmosphere. TMSBr (0.13 ml, 1 mmol) and $ZnI_2$ (3.4 mg, 0.01 mmol) were added. The reaction was stirred at r. t. for 4 hours, then it was shaken with a saturated aqueous solution of $NaHCO_3$ and the organic phase was separated by a separatory funnel, then the aqueous phase was extracted with ether. The combined organic extracts were washed with brine, dried over $MgSO_4$ and filtered. Removal of the solvents afforded a residue that was used immediately with no purification.

(13a): $^1$H-NMR δ 6.764 (2H, s, Ar), 5.456 (1H, s, olefin), 4.901 (1H, s, olefin), 4.752 (1H, s, olefin), 3.930-3.903 (2H, m, $CH_2Br$), 3.784-3.756 (1H, d, J=8.2 Hz, benzyl), 2.592-2.643 (2H, m,), 2.306 (6H, s, OAc), 2.198-2.131 (2H, t, J=10.2 Hz), 1.708 (3H, s, allyl $CH_3$), 1.698-1.472 (4H, m), 1.439-1.194 (5H, m), 0.090-0.865 (3H, t, J=5.3 Hz, terminal $CH_3$).

IR: 2900, 1750, 1360, 1200, 1020, 900, 720 $cm^{-1}$.

Example 22

(+)-7-Bromo-diacetate CBD DMH (13b)

Prepared with the same procedure reported for (13a).

(13b): $^1$H-NMR δ 6.816 (2H, s, Ar), 5.645 (1H, s, olefin), 4.557 (1H, s, olefin), 4.448 (1H, s, olefin), 4.016-3.966 (2H, m, $CH_2Br$), 3.483-3.405 (1H, m, benzyl), 2.655-2.459 (1H, m, allyl), 2.220 (6H, s, OAc), 1.883-1.637 (4H, m), 1.510 (3H, s, allyl $CH_3$), 1.485-1.426 (4H, m), 1.410-1.176 (10H, m), 1.010-0.995 (2H, m) 0.853-0.807 (3H, t, J=6.5 Hz, terminal $CH_3$).

IR: 2900, 1750, 1370, 1220, 1020, 900, 750 $cm^{-1}$.

Example 23

(+)-7-Nor-formyl-diacetate CBD (14a)

(13a) (100 mg, 0.21 mmol), 18-Crown-16 (55.4 mg, 0.21 mmol) and $K_2CrO_4$ (50.9 mg, 0.26 mmol) were dissolved in anhydrous HMPT (2 ml, distilled under vacuum and stored over 4A° molecular sieves). The mixture was stirred and heated at 110 C for 2 hours. The reaction was cooled and quenched by addition of 1 M HCl and the aqueous phase was extracted with ether. The organic phase was washed with brine, dried over $MgSO_4$ and filtered. Removal of the solvent under reduced pressure afforded a residue that was chromatographed on silica gel (20% Ether/PE.) to give 27.7 mg of the pure (14a) (yield 32%).

(14a): $^1$H-NMR δ 9.434 (1Hs CHO), 6.778 (2H, s, Ar), 6.638 (1H, s, olefin), 4.633 (1H, s, olefin), 4.489 (1H, s, olefin), 3.746-3.718 (1H, d, J=8.4 Hz, benzyl), 2.686-2.552 (4H, m), 2.304-2.075 (6H, br s), 1.965-1.921 (1H, m), 1.754-1.590 (6H, m), 1.318-1.305 (5H, m), 0.909-0.865 (3H, t, J=6.2 Hz, terminal $CH_3$).

IR: 2900, 1750, 1670, 1160, 1020 cm~

$[\alpha]_D$: +111.5 (c 3.5 mg/ml, $CHCl_3$)

Example 24

(+)-7-Nor-formyl-diacetate (14b)

Prepared with the same procedure reported for (14a), but the yield was slightly worse (28%).

(14b): $^1$H-NMR δ 9.420 (1Hs CHO), 6.861 (2H, s, Ar), 6.501 (1H, s, olefin), 4.611 (1H, s, olefin), 4.455 (1H, s, olefin), 3.705-3.671 (1H, m, benzyl), 2.667-2.552 (3H, m), 2.292-2.071 (6H, br s, OAc), 1.960-1.890 (2H, m), 1.601 (3H, s, allyl $CH_3$), 1.590-1.485 (4H, m), 1.241-1.711 (8H, m) 1.100-0.931 (2H, m) 0.854-0.865 (3H, t, J=5.7 Hz, terminal $CH_3$).

IR: 2900, 1750, 1660, 1160, 1020 $cm^{-1}$.

$[\alpha]_D$: +85.7° (c 1.4 mg/ml, $CHCl_3$)

Example 25

(+)-7-Nor-carboxy-diacetate CBD (15a)

$NaClO_2$ (80% pure 82.6 mg, 0.73 mmol) was added in small quantities to a stirred mixture of (14a) (70 mg, 0.17 mmol), 2-methyl-2-butene (0.45 ml, 4.25 mmol), a saturated aqueous solution of $KH_2PO_4$ (0.2 ml) in t-butanol (4 ml). The reaction was stirred at room temperature for 5 hours, and monitored by TLC (50% Ether/P. E.). Then water was added (20 ml) and the mixture was extracted several times with ethyl acetate. The organic phase was washed with brine, dried over $MgSO_4$ and filtered. Removal of the solvent under reduced pressure afforded a residue that was chromatographed on silica gel (30% Ether\PE.) to give 61.8 mg of the (25a) (yield 85%).

(15a): $^1$H-NMR δ 6.939 (1H, s, olefin), 6.770 (2H, s, Ar), 4.611 (1H, s, olefin), 4.462 (1H, s, olefin), 3.618-3.718 (1H, m, benzyl), 2.589-2.538 (3H, m, allyl+benzyl), 2.212 (6H, s, OAc), 1.961-1.862 (1H, m), 1.858-1.641 (1H, m), 1.592 (5H, br s), 1.321-1.255 (7H, m), 0.903-0.858 (3H, t, J=6.8 Hz, terminal $CH_3$).

IR: 3300, 2900, 1750, 1270, 1020 $cm^{-1}$.

Example 26

(+)-7-Nor-carboxy-diacetate CBD DMH (15b)

Prepared with the same procedure reported for (15a).

(15b): $^1$H-NMR δ 6.946 (1H, s, olefin), 6.854 (2H, s, Ar), 4.592 (1H, s, olefin), 4.436 (1H, s, olefin), 3.635-3.590 (1H, m, benzyl), 2.605-2.455 (1H, m, allyl), 2.208 (6H, s, OAc), 1.950-1.803 (2H, m), 1.795-1.610 (2H, m), 1.574 (3H, s, hallyl CH$_3$), 1.529-1.475 (4H, m), 1.267-1.174 (10H, m), 1.022 (2H, br s), 0.845-0.805 (3H, t, J=6.6 Hz, terminal CH$_3$).
IR: 3300, 2900, 1750, 1270, 1020 cm$^{-1}$.

Example 27

7-Nor-carboxy CBD (3a)

(15a) (50 mg, 0.12 mmol) was dissolved in ethanol (10 ml) and 1N NaOH (0.5 ml) was added and the reaction was refluxed for 1 hour. The ethanol was removed under reduced pressure, and the residue was diluted with water (20 ml) and the mixture was acidified with 2N HCl. The solution was extracted with ether. The combine organic extracts were washed brine, dried on MgSO$_4$ and filtered. Removal of the solvents under reduced pressure afforded a residue that was chromatographed on silica gel (30% Ether\ PE.) to give 38.2 mg of the (3a) (yield 95%).

(3a): $^1$H-NMR δ 7.085 (1H, s, olefin), 6.173 (2H, s, Ar), 4.604-4.566 (2H, d, J=11.4 Hz, olefin), 4.115-4.033 (1H, m, benzyl), 2.799-2.688 (1H, m, allyl), 2.623-2.541 (1H, m), 2.444-2.391 (2H, t, J=7.5 Hz), 1.950-1.869 (1H, m), 1.803-1.669 (5H, m), 1.623-1.453 (4H, m), 1.309-1.178 (5H, m), 0.902-0.857 (3H, t, J=6.5 Hz, terminal CH$_3$).
IR: 3350, 2950, 1700, 1440, 1400, 1160, 920, 740 cm$^{-1}$.
[α]$_D$: +112.3° (c 1.87 mg/ml, MeOH)

Example 28

(+)-7-Nor-carboxy CBD DMH (3b)

Prepared with the same procedure reported for (3a).
(3b): $^1$H-NMR δ 7.121 (1H, s, olefin), 6.291 (2H, s, Ar), 4.619-4.555 (2H, d, J=19.1 Hz, olefin), 4.036-4.033 (1H, d, J=8.9 Hz, benzyl), 2.718-2.567 (2H, m), 2.378-2.274 (1H, m), 1.948-1.904 (1H, m), 1.828-1.765 (1H, m), 1.648 (3H, s, allyl CH$_3$) 1.622-1.430 (4H, m), 1.236-1.189 (8H, m), 1.001-0.965 (2H, m), 0.878-0.837 (3H, t, J=6.2 Hz, terminal CH$_3$).
IR: 3330, 2900, 1700, 1420, 1160, 920, 740 cm$^{-1}$.
[α]$_D$: +86.7° (c 2.05 mg/ml, CHCl$_3$)

Example 29

Biological Activity of the Compounds

Central Nervous System

Mice were injected with antagonist 90 minutes before testing and/or with agonist 60 minutes before testing in a series of four assays which reflect central cannabinoid activity [Martin (1991) id. ibid.; modified by Fride, E. and R. Mechoulam (1993) id. ibid.]. This "tetrad" consists of, consecutively, ambulation and rearing in an open field (8 minutes), immobility on an elevated ring of 5 cm diameter (4 minutes), rectal temperature (Yellow Peripheral Nervous System a. Intestinal Motility Defecation was measured as the number of fecal pellets voided in the open field. In some experiments (as indicated below), fecal pellets and body temperature were assessed for a prolonged period (3 hr).

b. Arachidonic Acid Induced Inflammation of the External Ear

Ear inflammation was measured by assessing ear tissue swelling after topical application of arachidonic acid, as described previously [Hanus (1999) id. ibid.]. Briefly, at various times after i.p. drug injections, arachidonic acid was applied to the inner surface of one ear (4.5 mg dissolved in 5 μA ethanol). The opposite ear served as control (5 ethanol). Ear thickness was determined (in 0.01-mm units) by using a dial thickness gauge (Mitutoyo, Japan) every 15 minutes for 90 minutes, starting immediately after arachidonic acid application.

Pain: Central Vs. Peripheral

Pain perception on a hot plate, is considered to be mediated by a central mechanism whereas the second, late phase of the response to an implantar injection of formalin reflects inflammatory pain mechanisms [Tjolsen, A. and Hole (1997) id. ibid.].

Thus, central pain perception was assessed by the analgesic response on a hot plate (55° C., Columbus Instruments, OH, USA). Peripheral pain was measured by the response to implantar injection of formalin (4%) 45 minutes after injection of the drug.

Statistical Analyses

When 3 or more treatment groups were compared, data were analyzed with 1-way ANOVAs with Student Newman-Keul post-hoc tests. Two groups were analyzed with t-tests.

Results (+)-CBD, which weakly binds CB$_1$ and CB$_2$ receptors, had no central neither peripheral (intestinal motility) effects (FIG. 1). Although all of the (+)-CBD analogues showed substantial CB$_1$ receptor binding (see Table 1 and Bisogno et al., 2001), only (+)-7-OH-CBD-DMH had central effects in all assays of the tetrad (FIG. 2 and Table 1); (+)-CBD-DMH had a modest effect on rearing in an open-field (FIG. 2 and Table 1). The experiment was repeated using (+)-CBD-DMH at least 5 times, and absence of central effects or small effects, was always found, usually in one or two assays (see FIG. 3 for a comparison with Δ$^9$-THC).

However, all compounds, highly significantly inhibited defecation (almost always reducing fecal pellets to zero, see FIG. 4 and Table 1).

Centrally mediated pain in response to exposure to a hot plate (FIG. 5) was not affected by (+)-CBD-DMH. In contrast, the second, inflammatory phase of the formalin-induced pain response [Tjolsen et al., 1992], was almost completely inhibited by (+)-CBD-DMH (FIG. 6).

Arachidonic acid-induced inflammation of the external ear was almost completely inhibited by 40 (FIG. 7A) or 10 (FIG. 7B) mg/kg of (+)-CBD-DMH. (+)-CBD-DMH was as potent as indomethacin (FIGS. 7A-B). (+)-7-OHCBD-DMH (20 mg/kg) also inhibited ear inflammation, but (+)-CBD had no effect (FIG. 7C).

Receptor Mechanism: Effect of Antagonists and CB$_1$-/- Receptor Knockout Mice

The inhibition of defecation induced by (+) CBD-DMH, was almost fully reversed by SR141716A (FIG. 8), but not at all by 3 mg/kg SR1446528 (FIG. 9).

A lower dose of SR144528 (1 mg/kg), also did not prevent intestinal immotility induced by (+)-CBD-DMH (data not shown).

None of the drugs assessed ((+)-CBD-DMH, (+)-7-OH-CBD-DMH and Δ$^9$-THC had any effect in CB$_1$-/- receptor knockout mice, centrally (not shown) or peripherally on intestinal motility (FIG. 10).

TABLE 1

| Compound | CB1/CB2 Receptor Binding (Ki, μM) | Horizontal Movements (% MPE)[2] | Vertical Movements (% MPE)[2] | Catalepsy (Freezing of Movement) (% MPE)[2] | Analgesia (Hot Plate) (% MPE)[2] | Hypothermia (Δ-Body Temp.) (° C.)[2] | Inhibition of Intestinal Motility (% MPE)[2] |
|---|---|---|---|---|---|---|---|
| Δ9–THC | 0.046/0.320 | 44* | 12* | 44* | 97* | −2.1* | 100* |
| +CBD | 0.84/0.20[1] | 108 | 103 | 05 | 13 | 0.5 | 13 |
| +CBD-DMH | 0.017/0.21[1] | 82 | 61 | 16 | 10 | −0.3 | 100* |
| +7OH-CBD | 0.0053/0.101 | 107 | 81 | 0 | 77 | 0.3 | 89* |
| +7OH-CBD-DMH | 0.0025/0.044[1] | 01* | 0* | 95* | 100* | −5.2* | 100* |
| +COOH-CBD | 0.0132/0.322 | 80 | 71 | 06 | nd | −0.6 | 100* |
| +COOH-CBD-DMH | 0.0058/0.156 | 102 | 100 | 0 | 09 | 0.2 | 100* |

Legend:
Central and peripheral effects of Δ9–THC (−) and (+) CED and their analogues.
Female Sabra mice (8-12 weeks old) were injected at a time interval, which had been shown previously to yield maximal effects (30 or 60 min) before testing in a series of 6 consecutive assessments: motor activity (ambulation and rearing) and defecation (intestinal motility) in an open field (for 8 min); catalepsy on an elevated ring (for 4 min); response to a painful stimulus (hot plate kept at 55° C., mouse was allowed to remain on the plate for maximally 45 sec) and rectal temperature (hypothermia).
All groups consisted of 5 mice. All drugs were injected at 20 mg/kg in a mixture of Ethanol: Cremophor:Saline = 1:1:18 ("Vehicle").
Each compound was tested at least twice, with almost identical results; several compounds (such as (+) CBD DWH and (+) 7OH CBD DMH were tested more than 5 times.
[1]Data from Bisogno et al., 2001
[2]In order to compare between the pharmacological effects of the various compounds and their binding constants, the data from the tetrad and intestinal motility assays, were normalized using formula's: were normalized using various formula's:
Horizontal and vertical movements in the open field:

$$\% \text{ MPE} = 1 - \frac{\text{Vehicle} - \text{Experiment}}{\text{Vehicle}} \times 100\%$$

Immobility on a ring (catalepsy)

$$\% \text{ MPE} = \frac{\text{Experiment} - \text{Vehicle}}{240 - \text{Vehicle}} \times 100\%$$

Analgesia on a hot plate:

$$\% \text{ MPE} = \frac{\text{Experiment} - \text{Vehicle}}{45 - \text{Vehicle}} \times 100\%$$

Inhibition of intestinal motility:

$$\% \text{ MPE} = \frac{\text{Vehicle} - \text{Experiment}}{\text{Vehicle}} \times 100\%$$

*significantly different from vehicle controls (at least P < 0.05); nd = not determined.

The invention claimed is:

1. A pharmaceutical composition containing as active ingredient a compound of the formula:

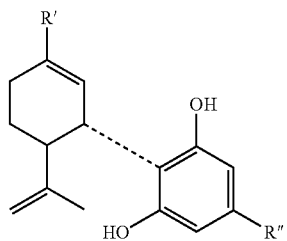

Formula I wherein:
R' designates a —COOH or —CH$_2$OH group, and
R" designates (i) a straight or branched C$_5$-C$_{12}$ alkyl group, or (ii) an —OR''' group wherein R''' designates a straight or branched C$_5$-C$_9$ alkyl group, or a straight or branched C$_5$-C$_9$ alkyl group substituted with a phenyl group on the terminal carbon atom, or (iii) a —(CH$_2$)$_n$—O—C$_{1-5}$ alkyl group, wherein n is an integer of from 1 to 7;
with the proviso that R' is not —CH$_2$OH when R" is pentyl or dimethylheptyl, and pharmaceutically acceptable salts and esters thereof and
further comprising at least one pharmaceutically acceptable carrier, additive, excipient or diluent.

2. The pharmaceutical composition of claim 1, comprising an additional pharmaceutically active agent.

3. The pharmaceutical composition of claim 1, wherein R' is —COOH and R" is a pentyl or dimethylheptyl group.

4. The pharmaceutical composition of claim 1 wherein the compound is an optically pure (+) enantiomer.

* * * * *